US011806484B2

(12) United States Patent
Mitchell et al.

(10) Patent No.: US 11,806,484 B2
(45) Date of Patent: Nov. 7, 2023

(54) CATHETER WITH HEAT TRANSFER MINIMIZING ANNULAR SPACE

(71) Applicants: Jennifer E. Mitchell, Elmer, NJ (US); Joseph R. Licwinko, Kenilworth, NJ (US); Thomas L. Merrill, Sewell, NJ (US)

(72) Inventors: Jennifer E. Mitchell, Elmer, NJ (US); Joseph R. Licwinko, Kenilworth, NJ (US); Thomas L. Merrill, Sewell, NJ (US)

(73) Assignee: FocalCool, LLC, Sewell, NJ (US)

( * ) Notice: Subject to any disclaimer, the term of this patent is extended or adjusted under 35 U.S.C. 154(b) by 1331 days.

(21) Appl. No.: 16/250,544

(22) Filed: Jan. 17, 2019

(65) Prior Publication Data

US 2022/0111175 A1    Apr. 14, 2022

Related U.S. Application Data

(60) Provisional application No. 62/619,151, filed on Jan. 19, 2018.

(51) Int. Cl.
*A61M 25/00*        (2006.01)
*A61M 25/01*        (2006.01)
(Continued)

(52) U.S. Cl.
CPC .... *A61M 25/0097* (2013.01); *A61M 25/0074* (2013.01); *A61M 25/0133* (2013.01);
(Continued)

(58) Field of Classification Search
CPC .......... A61M 25/0026; A61M 25/0028; A61M 25/0029; A61M 25/0097;
(Continued)

(56) References Cited

U.S. PATENT DOCUMENTS 2,967,152 A * 1/1961 Matsch ................ F17C 13/001
                                                         220/592.2
4,022,215 A   5/1977 Benson
(Continued)

FOREIGN PATENT DOCUMENTS

WO       200164145         9/2001
WO    WO-2005091810 A2 * 10/2005 ........... A61N 5/1002
(Continued)

OTHER PUBLICATIONS

Smith, Douglas M. et al. "Aerogel-based thermal insulation". Journal of non-crystalline solids 225. Sep. 1, 1998. Abstract.
(Continued)

*Primary Examiner* — Kami A Bosworth

(57) ABSTRACT

A catheter configured to provide a delivery system for standard interventional devices and for rapid localized deep cooling to organs at risk of ischemia-reperfusion injury during procedures such as intracranial thrombectomy or emergency thrombectomy. The catheter is comprised of an insulative shaft with a multi-component braided outer lumen and an internal floating inner lumen with a plurality of structures configured to minimize contact and resulting heat transfer between the two lumens.

4 Claims, 24 Drawing Sheets

(51) Int. Cl.
   *A61M 39/10* (2006.01)
   *A61M 25/09* (2006.01)
(52) U.S. Cl.
   CPC ....... *A61M 39/105* (2013.01); *A61M 25/0054* (2013.01); *A61M 2025/091* (2013.01); *A61M 2205/32* (2013.01); *A61M 2205/3633* (2013.01)
(58) Field of Classification Search
   CPC .. A61M 2025/0004; A61M 2025/0039; A61M 2025/0059; A61M 2025/006; A61M 2205/3606; A61M 2205/3633
   See application file for complete search history.

(56) References Cited

U.S. PATENT DOCUMENTS

| | | | |
|---|---|---|---|
| 4,202,336 | A | 5/1980 | van Gerven |
| 6,042,559 | A | 3/2000 | Dobak, III |
| 6,428,563 | B1 | 8/2002 | Keller |
| 6,488,659 | B1 | 12/2002 | Rosenman |
| 6,685,732 | B2 | 2/2004 | Kramer |
| 6,758,857 | B2 | 7/2004 | Cioanta et al. |
| 7,211,066 | B1 | 5/2007 | Merrill |
| 7,306,589 | B2 | 12/2007 | Swanson |
| 7,388,089 | B2 | 6/2008 | Valenzuela et al. |
| 8,343,097 | B2 | 1/2013 | Pile-Spellman et al. |
| 8,353,942 | B2 | 1/2013 | Merrill |
| 8,740,892 | B2 | 6/2014 | Babkin et al. |
| 9,463,113 | B2 | 10/2016 | Pile-Spellman et al. |
| 9,737,686 | B2 | 8/2017 | Trainer et al. |
| 2002/0156451 | A1* | 10/2002 | Lenker ................ A61M 5/44 604/500 |
| 2003/0158514 | A1* | 8/2003 | Tal ................ A61M 25/0606 604/39 |
| 2005/0038413 | A1* | 2/2005 | Sansoucy .......... A61M 25/0075 604/537 |
| 2005/0124918 | A1* | 6/2005 | Griffin ................ A61M 25/01 600/585 |
| 2007/0010847 | A1* | 1/2007 | Pepper .............. A61M 25/1036 604/103.04 |
| 2007/0208323 | A1* | 9/2007 | Gregorich ......... A61M 25/0023 604/523 |
| 2012/0123509 | A1 | 5/2012 | Merrill et al. |
| 2014/0358136 | A1 | 12/2014 | Kelly et al. |
| 2016/0045719 | A1* | 2/2016 | Ha ................... A61M 25/0023 606/196 |
| 2017/0311789 | A1 | 11/2017 | Mulcahey et al. |

FOREIGN PATENT DOCUMENTS

| | | | |
|---|---|---|---|
| WO | WO-2008058132 A2 * | 5/2008 | .......... A61M 1/3659 |
| WO | 2017113971 | 7/2017 | |

OTHER PUBLICATIONS

PCT/US2019/035484. International Search Report and Written Opinion, dated Sep. 22, 2019.

Chen J et al. "Endovascular Hypothermia in Acute Ischemic Stroke: Pilot Study of Selective Intra-Arterial Cold Saline Infusion." Stroke. Apr. 28, 2016. pp. 1933-1935.

Mialek K et al. "Knudsen Self- and Fickian Diffusion in Rough Nanoporous Media." Physical Chemistry and Molecular Thermodynamics. pp. 1-43.

Merill T et al. "Design of a Cooling Guide Catheter for Rapid Heart Cooling." Journal of Medical Devices. Aug. 31, 2010. pp. 035001-1-035001-8.

Ovesen C et al. "Feasibility of Endovascular and Surface Cooling Strategies in Acute Stroke." Acta Neurologica Scandinavia. Oct. 31, 2012. pp. 399-405.

http://www.mddionline.com/article/design-considerations-small-diameter-medical-tubing. Jun. 23, 2016. pp. 1-3.

Mattingly T et al. "Catheter Based Selective Hypothermia Reduces Stroke Volume During Focal Cerebral Ischemia in Swine." JNIS. Feb. 12, 2015. pp. 418-422.

Mattingly T et al. "Cooling Catheters for Selective Brain Hypothermia." AJNR. May 2016. p. E45.

Thapliyal P et al. "Aerogels as Promising Thermal Insulating Materials: An Overview." Journal of Materials. Apr. 27, 2014. pp. 1-10.

Wu C et al. "Safety, Feasibility, and Potential Efficacy of Intraarterial Selective Cooling Infusion for Stroke Patients Treated with Mechanical Thrombectomy." Journal of Cerebral Blood Flow and Metabolism. Jun. 17, 2018. pp. 1-10.

PCT/US2019/035484. International Preliminary Report on Patentability, dated Jun. 16, 2021.

* cited by examiner

CATHETER WITH HEAT TRANSFER MINIMIZING ANNULAR SPACE

CROSS-REFERENCE TO RELATED APPLICATION

The present application claims priority from U.S. Provisional Patent Application Ser. No. 62/619,151, filed on Jan. 19, 2018, which is incorporated herein by reference in its entirety.

STATEMENT OF GOVERNMENT INTEREST

This invention was made with government support under Grant No. 1R43NS095573-01A1 awarded by The National Institutes of Health. The government has certain rights in the invention.

BACKGROUND OF THE INVENTION

Field of the Invention

The invention relates to a medical device used to reduce tissue injury resulting from ischemia, occurring naturally, through trauma, or from surgery. The invention also allows the application of adjunctive therapies such as angioplasty, stent placement, and intracranial thrombectomy.

Description of Related Art

Tissue in the human body is regulated at a constant temperature of approximately 37 degrees C. An essential part of this regulation is achieved by adequate perfusion of body fluids. Blood perfusion carries out many functions in addition to heat exchange, namely oxygenation of tissue. Without blood perfusion and therefore oxygen delivery, tissue becomes ischemic. This can occur during acute ischemic injury, such as stroke, heart attack, organ transplantation, spinal injury, or within the course of an initial injury, such as brain swelling after trauma, or reperfusion of occluded coronary/cerebral arteries.

Experimental evidence has shown that reductions in tissue temperature can reduce the effects of ischemia. Among other mechanisms, hypothermia decreases tissue metabolism, concentrations of toxic metabolic byproducts, and suppresses the inflammatory response in the aftermath of ischemic tissue injury. Depending on the time of initiation, hypothermia can be intra-ischemic, post-ischemic, or both. Hypothermic ischemic protection is preventive if tissue metabolism can be slowed down, and may enhance recovery by ameliorating secondary tissue injury or decreasing ischemic edema formation. Since the metabolic reduction is less than 10% per degree Celsius, only deep hypothermia targeting 20-25 degrees Celsius, conceivably provides adequate tissue protection via metabolic slowdown. Secondary tissue injury, thought to be mainly caused by enzymatic activity, is greatly diminished by mild to moderate hypothermia targeting 32-35 degrees Celsius. As early as 24 hours after onset of ischemia, secondary tissue injury can set off a mass effect with detrimental effects on viable surrounding tissues. Late post-ischemic hypothermia decreases edema formation and may therefore salvage tissue at risk.

To harness the therapeutic value of hypothermia the primary focus thus far has been on systemic body surface or vascular cooling, only a few concepts have embarked on local, tissue specific or cerebrospinal fluid cooling. Systemic cooling has specific limitations and drawbacks related to its inherent unselective nature. For example, research has shown that systemic or whole body cooling may lead to cardiovascular irregularities such as reduced cardiac output and ventricular fibrillation, an increased risk of infection, and blood chemistry alterations. Local cooling approaches have been limited by the technological challenges related to developing tiny heat exchangers for small arterial vessels. These vessel inner diameters are 6 mm and smaller.

While hypothermia technologies have been progressing, the field of endovascular neurological intervention has also grown. Today therapeutic devices include stent placement, angioplasty, direct thrombolytic infusion, and mechanical devices for clot removal, known as intracranial thrombectomy. In each of these therapeutic environments, ischemia-reperfusion damage is the focus. Boot-strapping local arterial based cooling together with these other emerging technologies will offer the patient optimal medical care. To accomplish this however, requires a unique cooling catheter system that not only cools effectively but also allows a pathway for the additional endovascular tools mentioned above.

Most related endovascular cooling catheter patents employ external passive transport enhancement techniques, where a fixed or static cooling catheter is placed inside a stagnant or moving body fluid. Passive techniques are transport enhancement approaches that do not add mixing energy to the fluid system of interest. They are particularly effective when fluid pumping power is not limited or prohibitive in cost. The approach involves adding surface area and/or inducing turbulence adjacent to the effective exchange surface area. These approaches are used throughout the heating and air conditioning industry where fluid pumping power or hydraulic energy can easily be adjusted. This differs, however, from the human body where physiological constraints naturally limit the hydraulic energy or fluid pumping power. In turn, aggressive passive enhancement techniques, particularly in small vessels, vessels that lead to individual organs like the brain, spinal cord, or kidney, are likely to lead to substantial blood side flow resistance that will likely affect cardiac output and or organ perfusion.

Prior art endovascular cooling techniques have one or more of the following disadvantages:

a) These techniques use devices that are sized for the vena cava, not organ specific arteries.

b) These techniques do not have dedicated adjunctive therapy pathways. Since the device designs are built for the venous applications, adjunctive therapies are less likely or common. As a result, these designs do not integrate well with existing endovascular tools for organ arteries nor do they offer pathways for adjunctive therapies.

c) These techniques do not target specific organs by minimizing systemic cooling via carefully chosen insulation techniques and pathways.

It would be beneficial to provide a cooling catheter that solves these limitations.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention provides several embodiments of insulative Knudsen-Effect catheter with minimized eccentricity. Each embodiment comprises a rear external hub used to connect the device to an outside control console, a hub strain relief, an insulative shaft, and a distal section that is flexible, atraumatic, and radiopaque. The inner lumen is sized for passage of microcatheters, guidewires, and similar interventional tools as well as therapeutic agents. The outer lumen is sized to either act as a guide catheter for other interventional tools or sized to pass within existing guide catheters. Two specific interventions are of interest: emergency angioplasty and intracranial thrombectomy. Additionally, any procedure that requires deep penetration into the body and may be enhanced with temperature control is amenable to the present invention. All of the embodiments have a concentric pathway configuration with an insulative or heat transfer minimizing annular space.

Accordingly the invention provides rapid, localized, deep cooling to ischemic organs without significant reductions in blood perfusion or vessel wall damage. "Deep cooling" is considered below 32° C., a temperature at which whole body cooling is normally deemed unsafe.

Further, the present invention provides a catheter that has a lumen body having a distal end and a proximal end. A hub is connected to the proximal end. The hub includes a luer connection and a vacuum port assembly.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
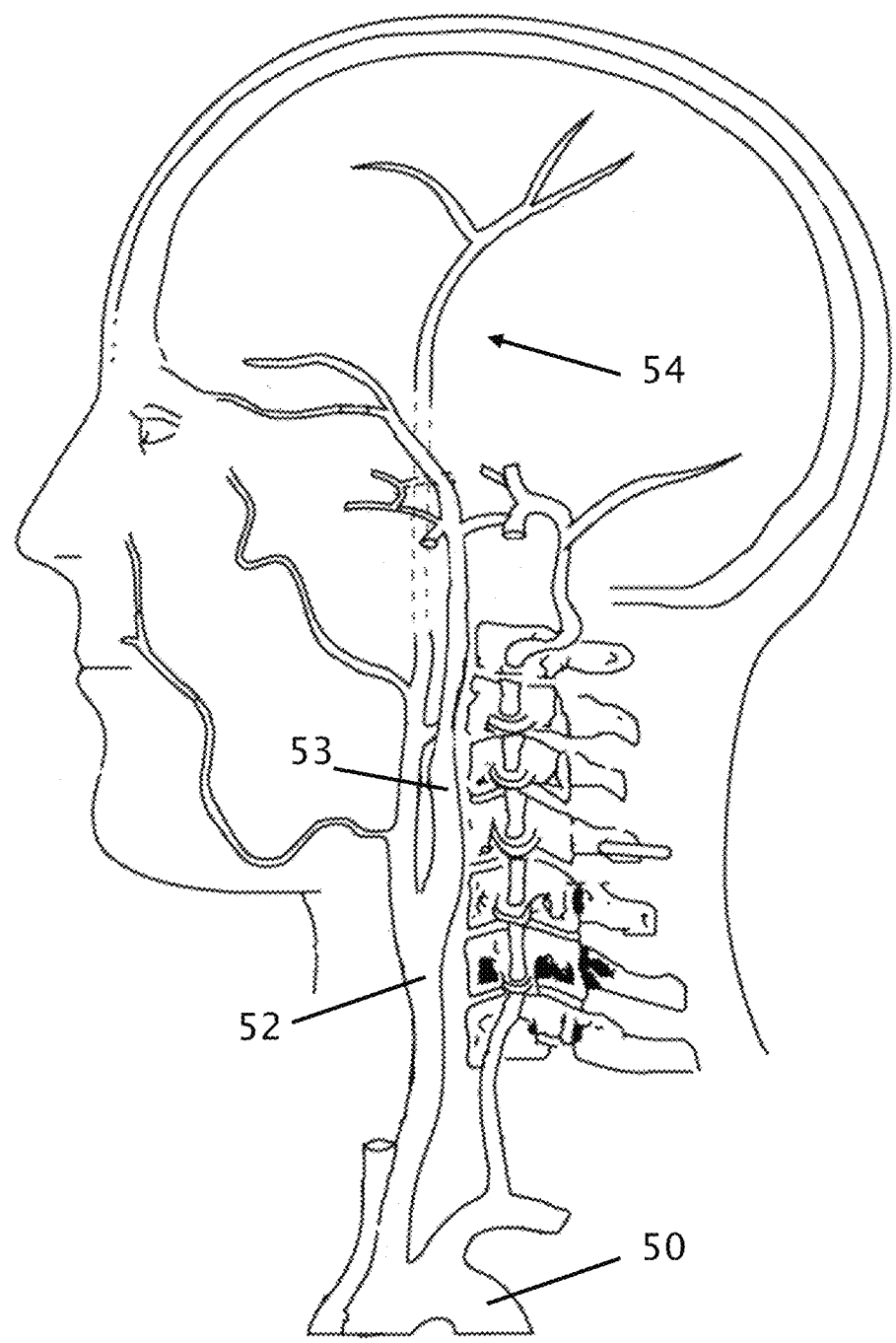
FIG. 1 shows a lateral view of the carotid artery and cranial blood vessels.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" is intended to mean a direction closer to a user of the inventive catheter and the term "distal" is intended to mean a direction farther from the user of the inventive catheter.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As shown in the Figures, in one embodiment, the present invention is an insulative catheter that is used to provide infusate, such as a cooling fluid, to small arteries, such as cranial or cardiac arteries. The infusate is used to cool the cells in an area where an aneurysm, a stroke, a myocardial infarction, or other traumatic event, has occurred, thereby slowing the body's metabolism in and around the affected area, and providing additional time for medical personnel to treat the affected area before irreparable damage occurs.

Figure 2:
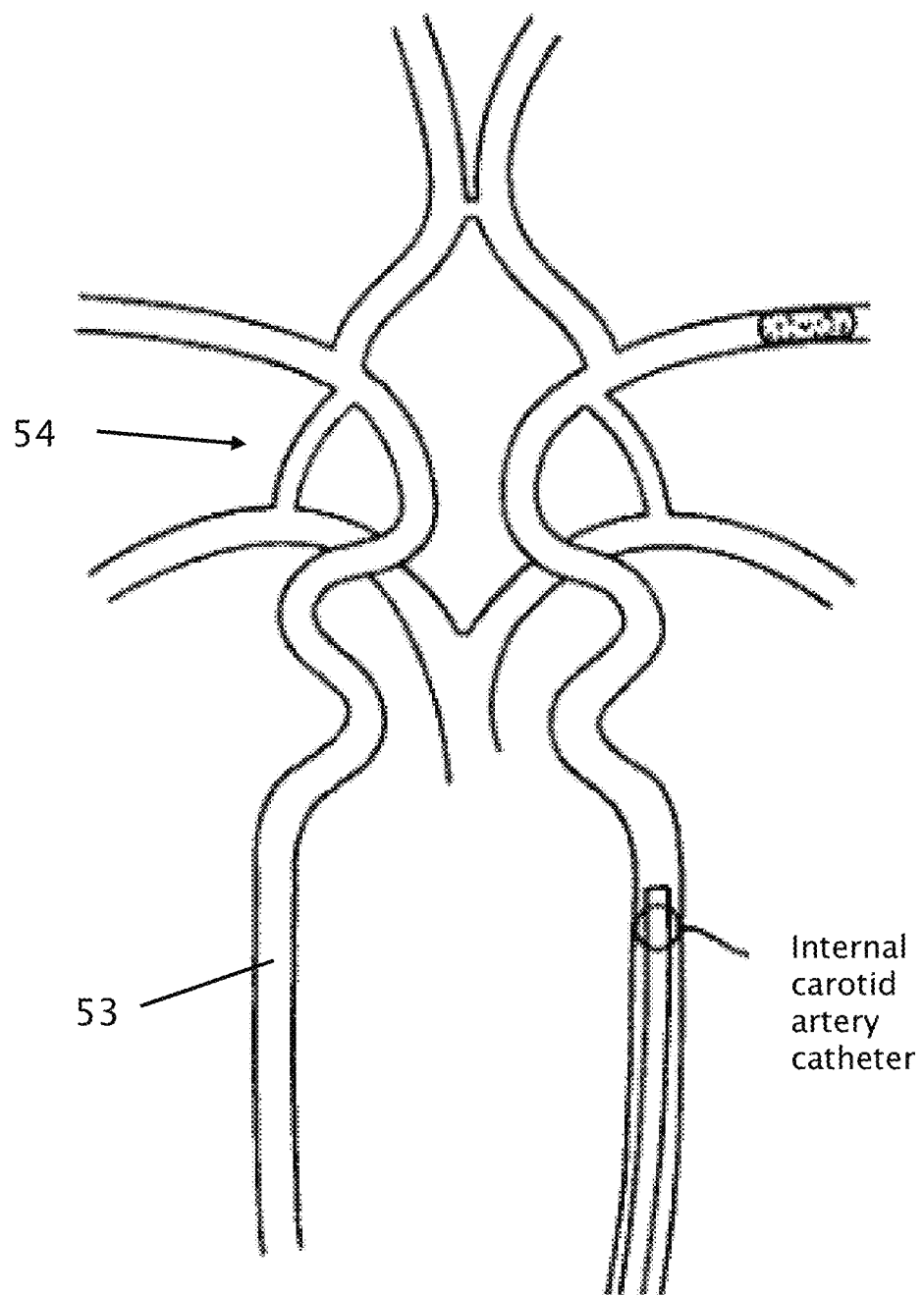
FIG. 2 shows an enlarged view of the carotid artery and cranial blood vessels taken from FIG. 1.
Figure 3:
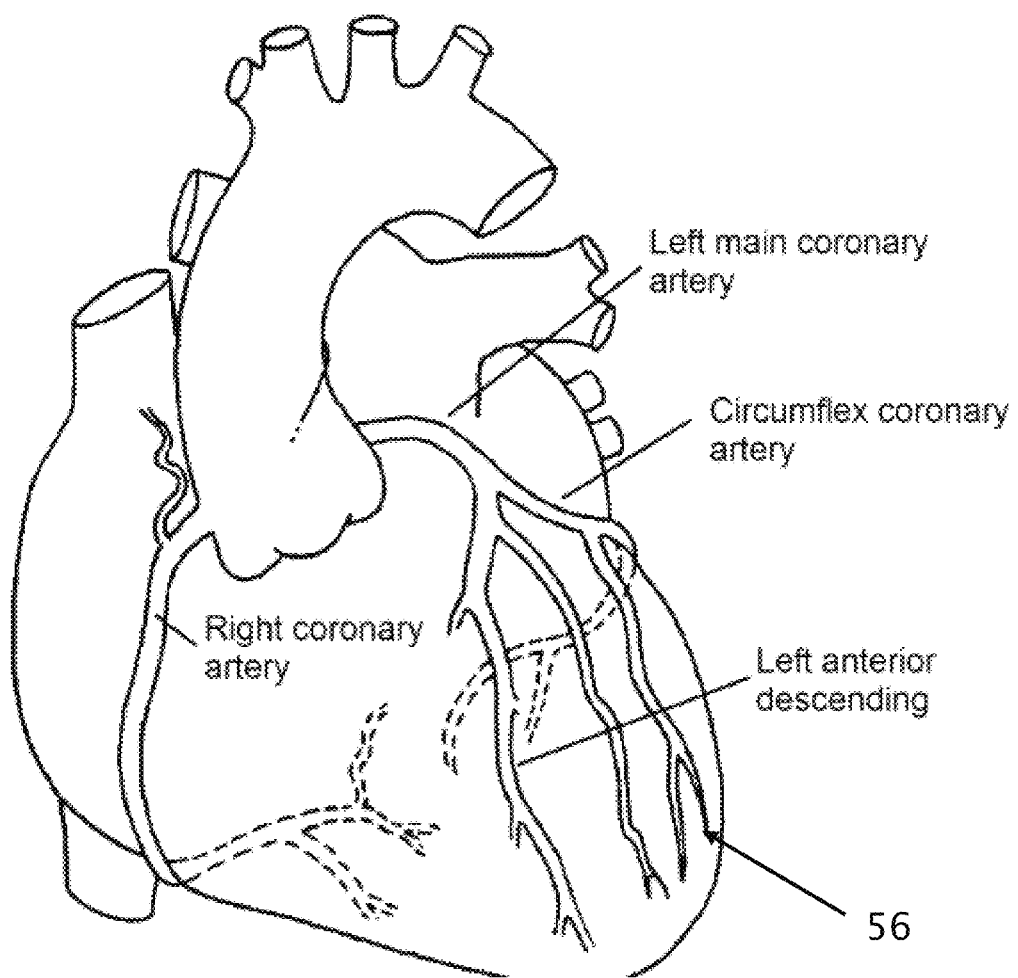
FIG. 3 shows an anterior view of a heart and the coronary arteries on the heart.

FIGS. 1-3 show the physiological landscape where a catheter according to the present invention can be used. FIG. 1 shows the aorta 50, with blood flow (shown by the arrow) into the external carotid artery 52 and subsequently to cranial arteries 54. The inner diameter of the common carotid artery 52 ranges from 6 to 8 mm and its length ranges from 8 to 12 cm. FIG. 2 is a close-up view of the neck and cranial arteries, including the internal carotid artery 53. The coronary arteries 56, shown in FIG. 3 are significantly smaller, with proximal inner diameters ranging from 2 to 3.5 mm and length ranging from 2 to 4 cm. The distal end of the inventive catheter is required to be able to be advanced through the larger of these arteries into the smaller of these arteries to deliver the infusate.

Figure 4:
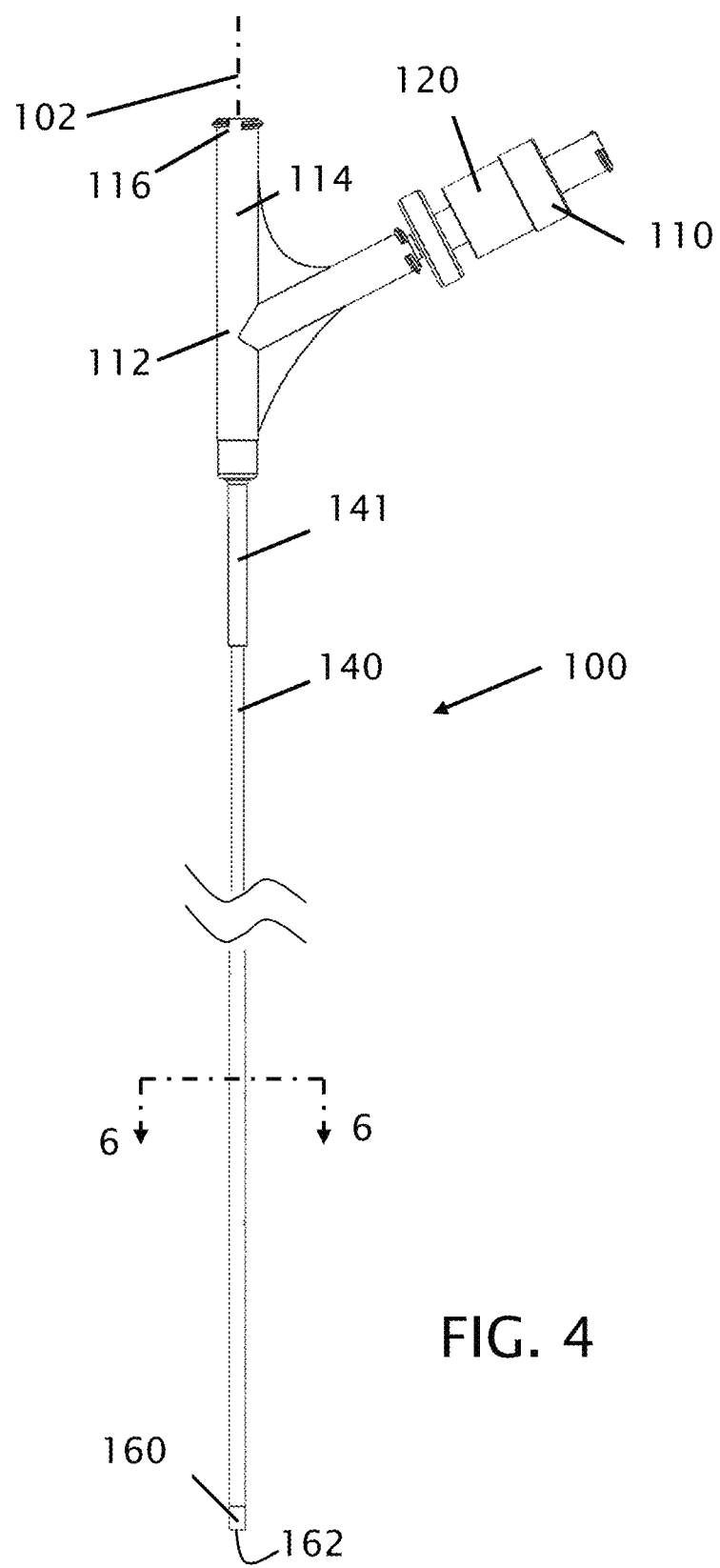
FIG. 4 shows a perspective view of an insulating catheter according to an exemplary embodiment of the present invention.
Figure 5:
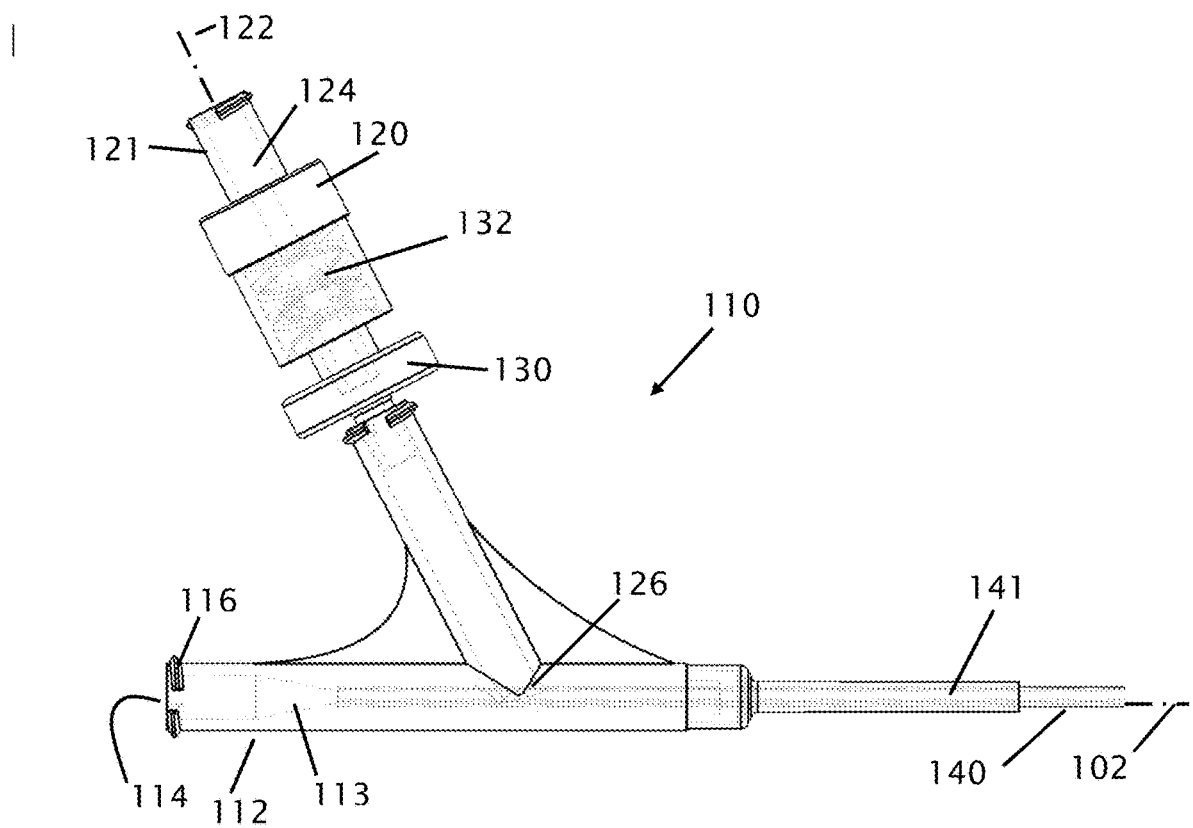
FIG. 5 is a side elevational view of a proximal end of the catheter of FIG. 4.
Figure 6:
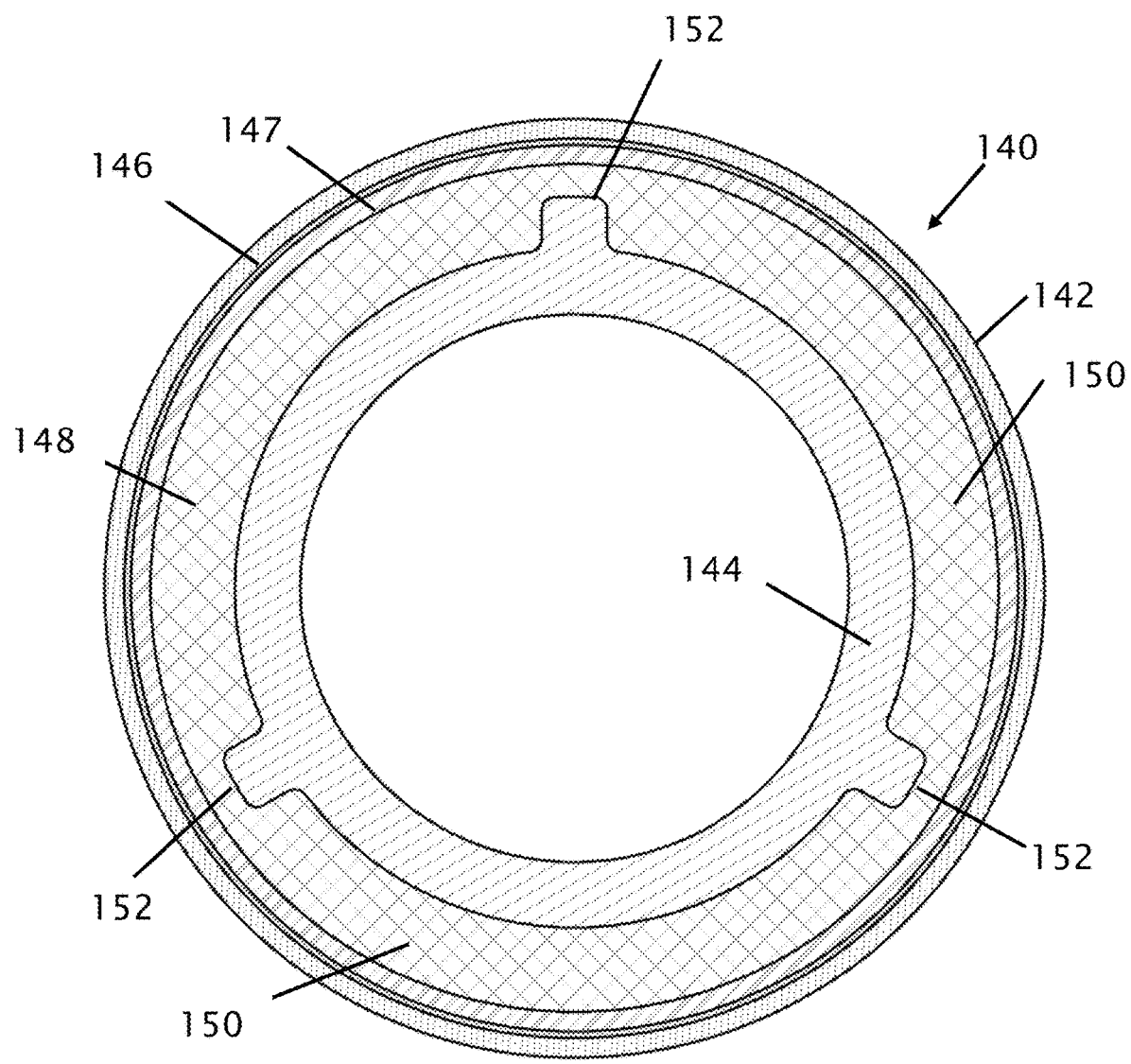
FIG. 6 is a sectional view of a distal end of the catheter of FIG. 4 taken along lines 6-6 of FIG. 4.

Referring now to FIGS. 4 and 5, a catheter assembly 100 according to an exemplary embodiment of the present invention is shown. Catheter assembly 100 extends along a longitudinal axis 102 and includes, from a proximal end to a distal end, a connection hub 110, an elongate body 140 extending distally from hub 110, and a distal tip 160 at the distal end of body 140.

The connection hub 110 connects the catheter assembly 100 to external systems such a cooling console (not shown) that is used to pump infusate into and out of the catheter assembly 100 and pre-existing interventional tools such as dilation catheters and stents (not shown). The connection hub 110 includes a hub base 112 having a though-passage 113 extending along the longitudinal axis 102. A proximal end 114 of the hub base 112 can include a luer connection 116 for removable connection to standard luer fittings.

Body 140 is connected to a distal end of hub 110 and carries infusate from hub 110 to distal tip 160 for discharge into a blood vessel. A strain relief 141 provides a solid connection between hub 110 and body 140. In an exemplary embodiment, body 140 can be between about 80 and 150 centimeters long although those skilled in the art will recognize that body 140 can be other lengths as well. Body 140 is insulated to reduce the amount of heat transfer between the exterior of catheter 100 and the infusate as the infusate flows through body 140.

Referring to FIGS. 6-10, a first embodiment of lumen designs for body 140 is shown. Body 140 includes an outer lumen or jacket 142 and an inner lumen 144. Outer lumen 142 is generally tubular in cross section, with a reinforcing coil or braid 146 molded therein and extending the length of body 140. Reinforcing coil 146 is used to reduce the kinking of body 140 as catheter 100 is advanced through blood vessels. An inner liner 147 defines an inner perimeter of outer lumen 142. In an exemplary embodiment, outer lumen 142 is constructed from Polyether block amide or Pebax®, although those skilled in the art will recognize that other materials can be used. The inner liner 147 can be constructed from Polytetrafluoroethylene or "PTFE".

Inner lumen 144 is generally tubular in cross section, with an inner volume that is circular in cross section with smooth walls to enhance the flow of infusate through lumen 144. The inner volume is in fluid communication with the luer connection 116 so that fluid provided to catheter assembly 100 via luer connection 116 flows through the inner volume for discharge from distal tip 160.

To minimize heat transfer between outer lumen 142 and inner lumen 144, it is desired to eliminate or at least reduce contact between outer lumen 142 and inner lumen 144. To accomplish this, an insulator 150 is provided in the space 148 between outer lumen 142 and inner lumen 144. The insulator 150 acts as a thermal barrier between the outer lumen 142, which is in contact with the patient's bodily fluids, which can be at a temperature of about 37 degrees Celsius, and the infusate in the inner lumen 144, which can be at a temperature as cold as −2 degrees Celsius.

An exemplary insulator 150 can be Enova® aerogel, manufactured by Cabot Corp., located in Billerica, Mass. Aerogel can be provided in powder form and has a particle size range between about 1 micron and about 120 micron, with a pore size of around 20 nm, and with a thermal conductivity of about 0.012 W/m° K at 25 degrees Celsius. To further enhance the insulative properties of the insulator 150, space 148 is in a vacuum, with a pressure of less than about 300 mbar absolute.

Figure 7:
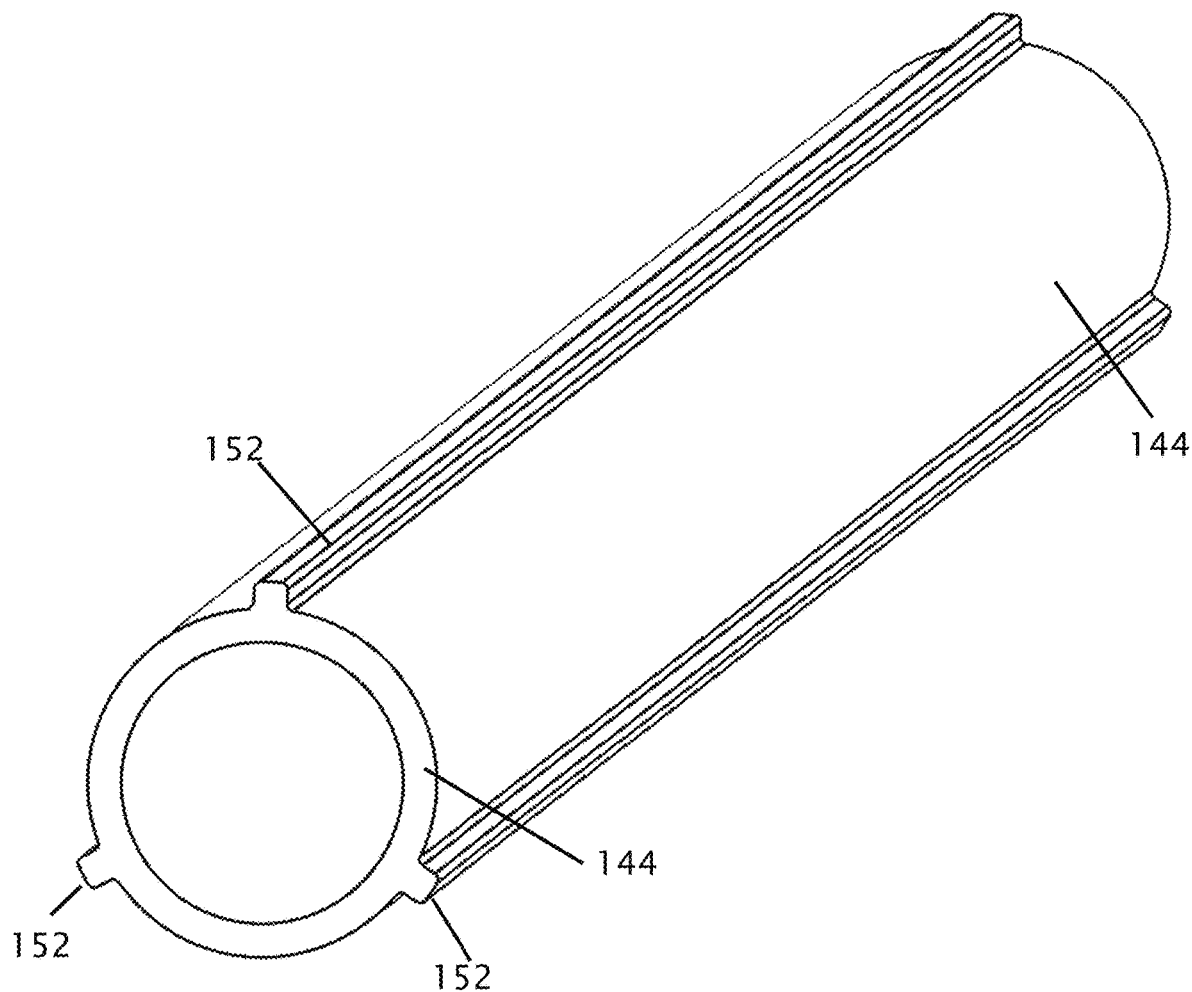
FIG. 7 is a perspective view of a first exemplary embodiment of an inner lumen for insertion within the outer lumen.
Figure 8:
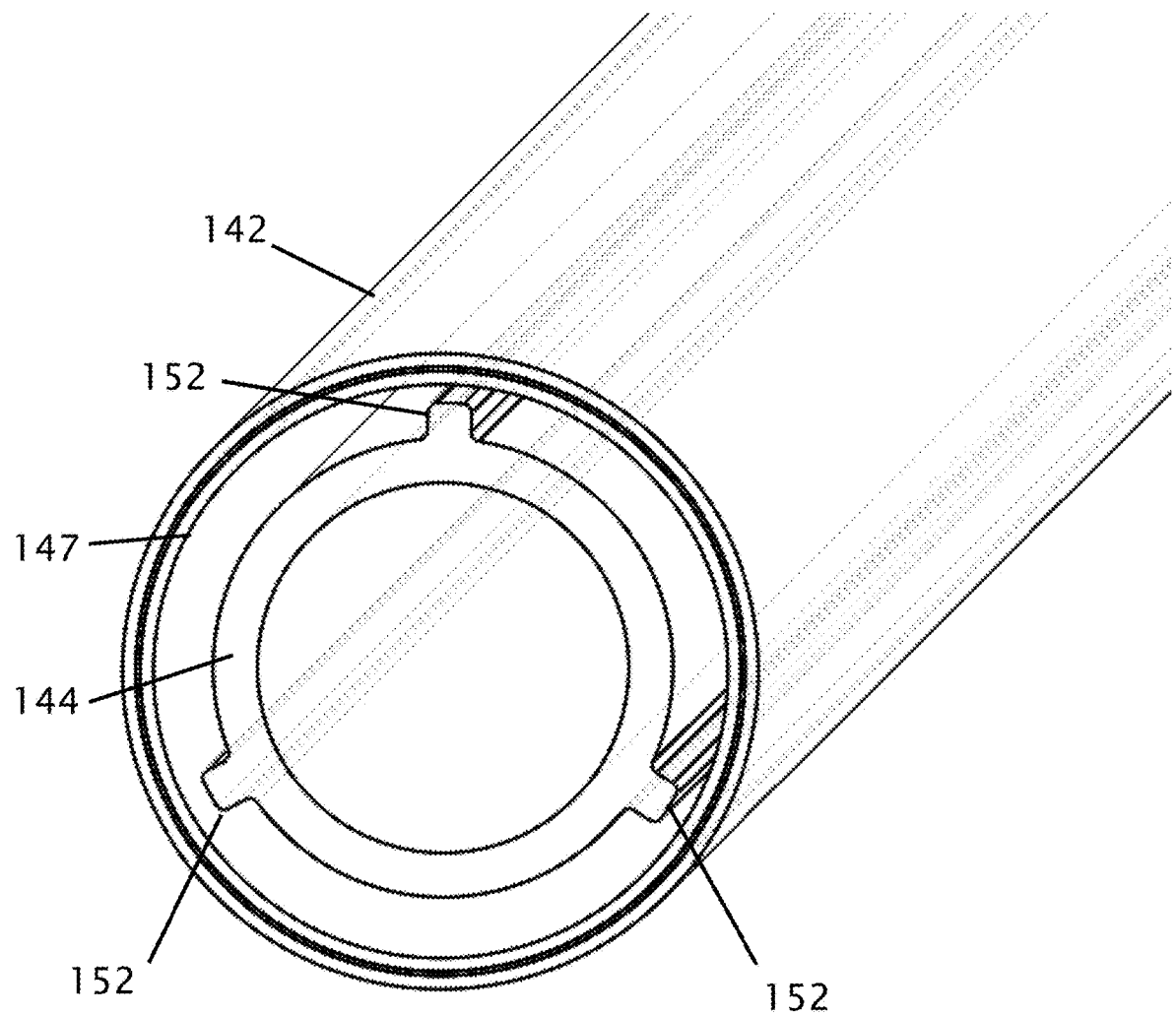
FIG. 8 is a distal elevational view of the catheter of FIG. 4, showing the inner lumen of FIG. 7 centrally located within an outer lumen.
Figure 9:
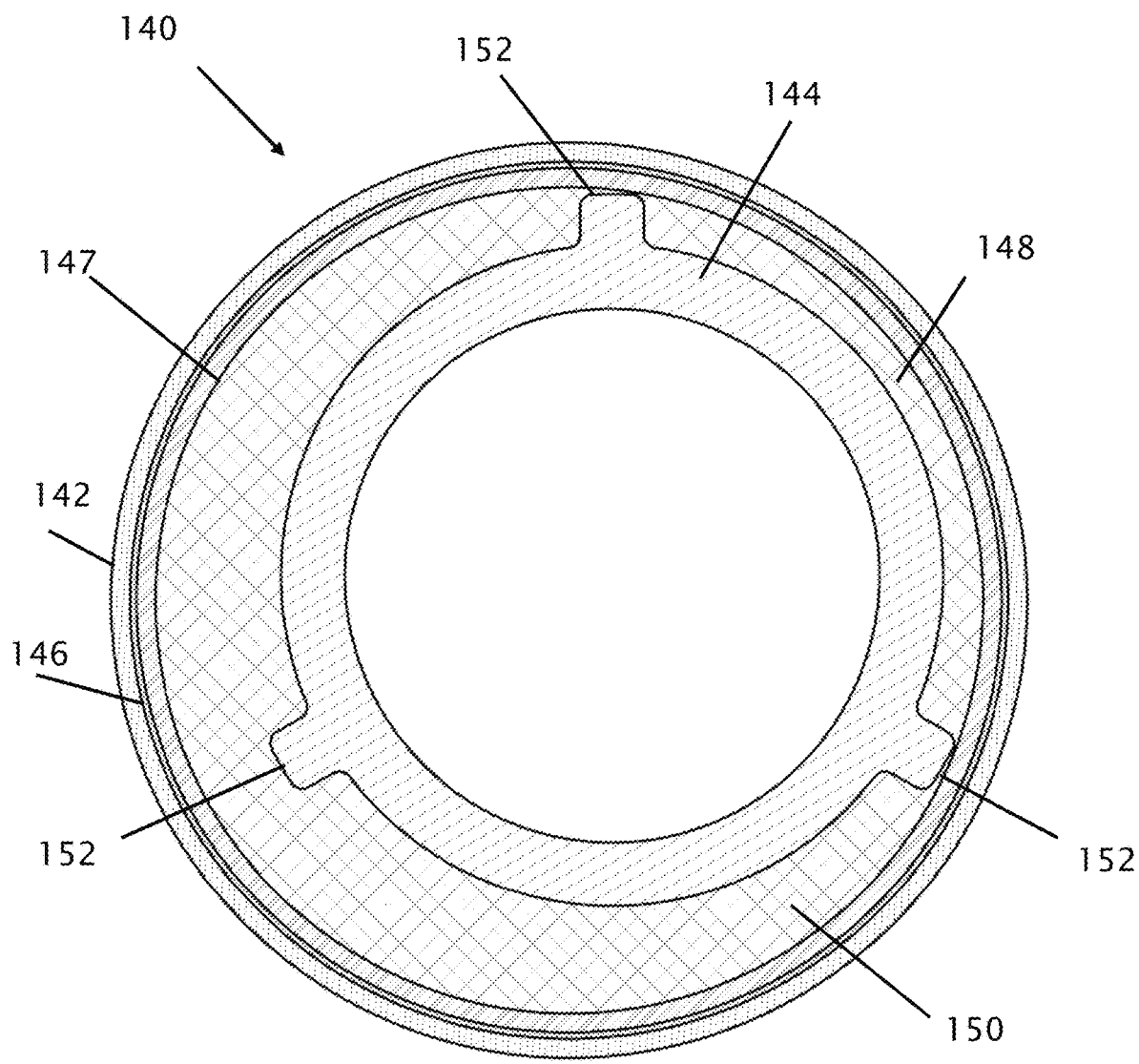
FIG. 9 is a distal elevational view of the catheter of FIG. 4, showing the inner lumen of FIG. 7 in a first eccentric position within the outer lumen.

Inner lumen 144 has a small enough outer diameter relative to the inner diameter of outer lumen 142 such that inner lumen 144 can "float" within outer lumen 142. Ideally, inner lumen 144 is centered within the space 148 to minimize heat transfer between body fluids or tissue and infusate. However, in reality, inner lumen 144 will likely engage the inner liner 147 of outer lumen 142, resulting in at least some conductive heat transfer between the lumens 142, 144. To minimize the amount of contact area, inner lumen 144 can include a plurality of raised ribs 152 extending radially outwardly from inner lumen 144. Ribs 152 have a generally rectangular cross section. As shown in FIG. 7, ribs 152 can extend the entire length of inner lumen 144. Alternatively, ribs 152 can extend in smaller sections along the length of inner lumen 144, with distances along the length of inner lumen 144 that are free of any ribs 152. In an exemplary embodiment, three ribs 152 are provided and are evenly spaced about 120 degrees such that, in the event that inner lumen 144 is eccentrically located within outer lumen 142 as shown in FIGS. 8 and 9, only corner edges of no more than two of the ribs 152 engage the inner wall of outer lumen 142 with linear contact, thereby minimizing the area of contact between inner lumen 144 and outer lumen 142, and minimizing heat transfer from outer lumen 142 to inner lumen 144.

Figure 10:
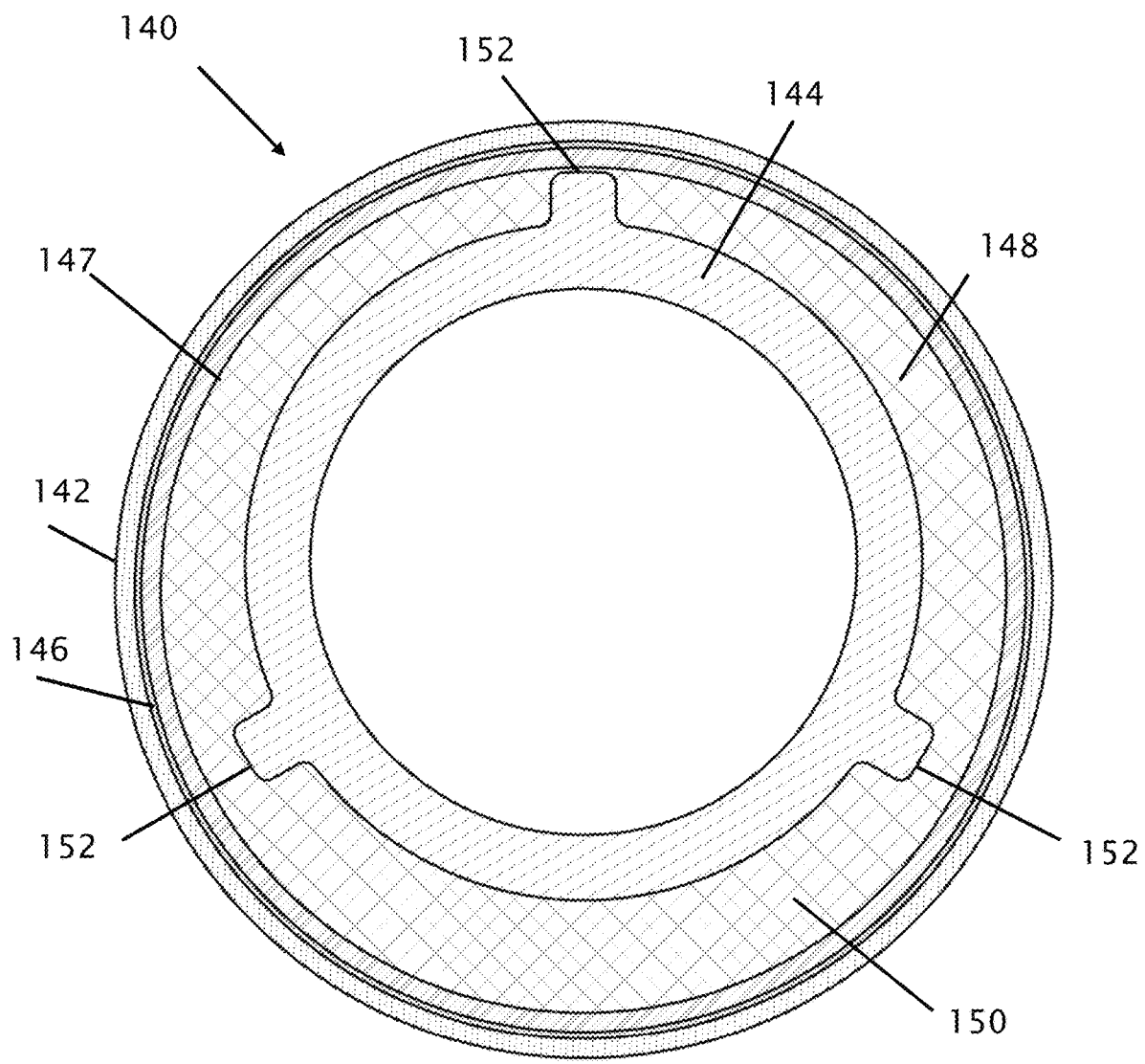
FIG. 10 is a distal elevational view of the catheter of FIG. 4, showing the inner lumen of FIG. 7 in a second eccentric position within the outer lumen.

FIG. 10 shows an alternative eccentric configuration of inner lumen 144 within outer lumen 142 such that only a single rib 152 engages the inner wall of outer lumen 142, also providing a small area of contact between inner lumen 144 and outer lumen 142.

Figure 11:
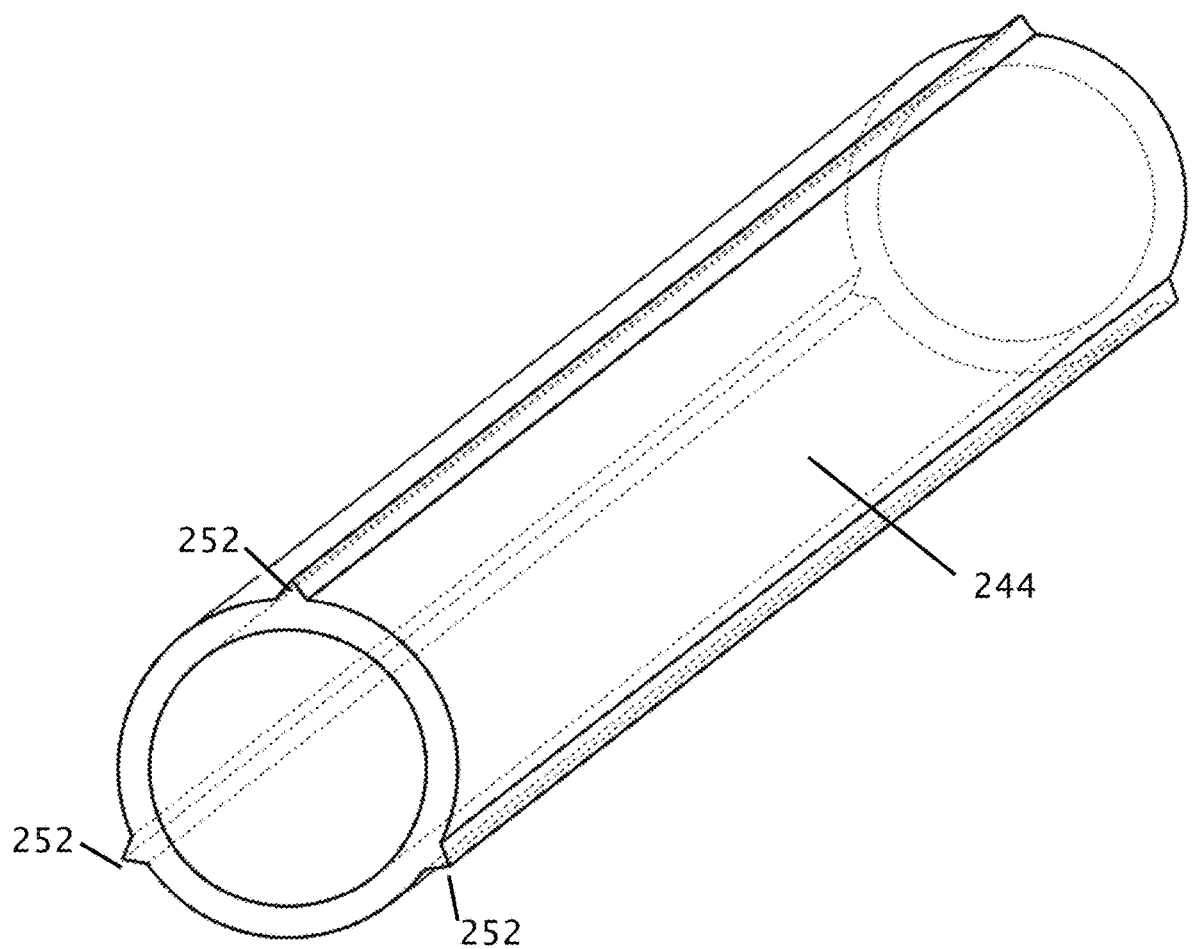
FIG. 11 is a perspective view of a second exemplary embodiment of an inner lumen for insertion within the outer lumen.
Figure 12:
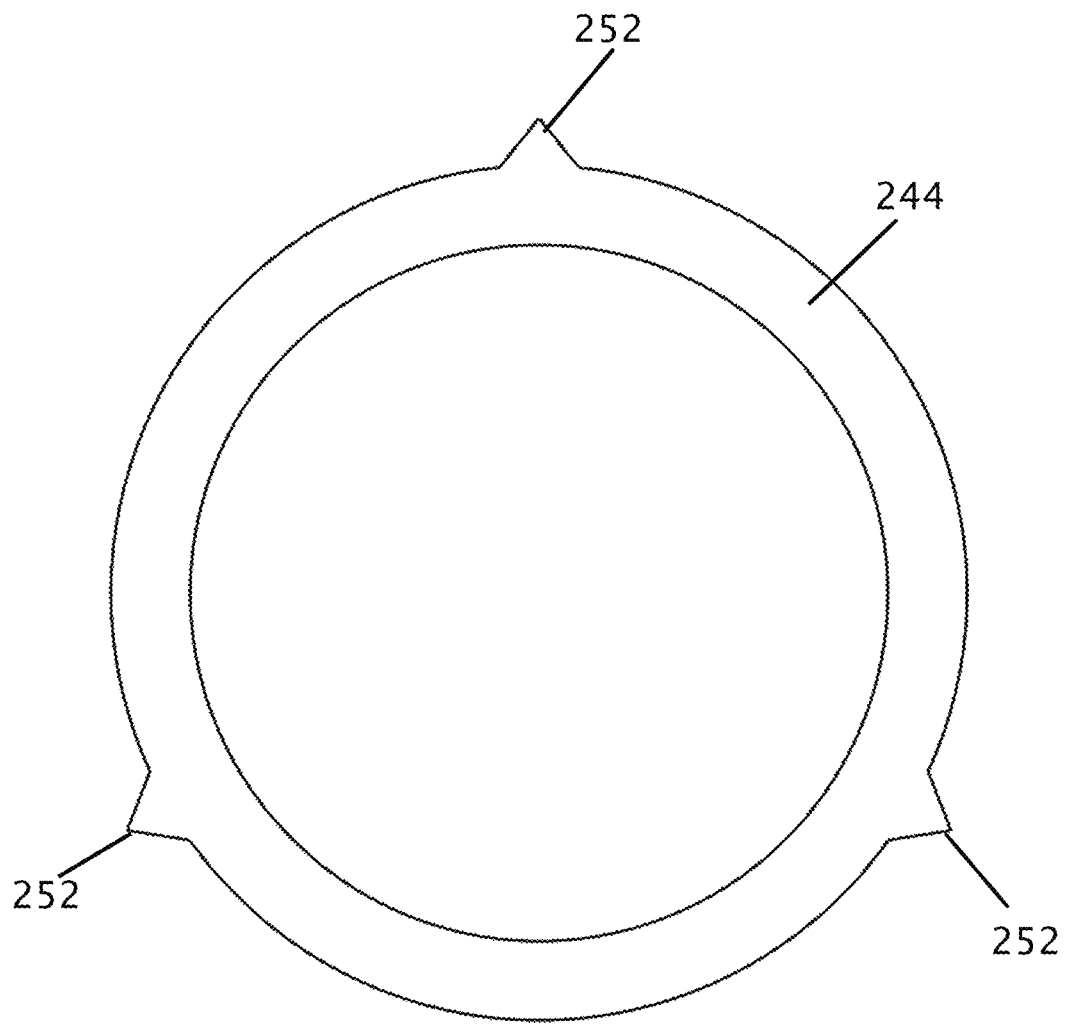
FIG. 12 is a side elevational view of the inner lumen of FIG. 11.

Alternative embodiments of rib designs for inner lumens are provided in FIGS. 11-20. FIGS. 11 and 12 show an inner lumen 244 having ribs 252 with triangular shaped cross sections. Similar to inner lumen 144, inner lumen 244 has a small enough outer diameter relative to the inner diameter of outer lumen 142 such that inner lumen 244 can "float" within outer lumen 142. When inner lumen 244 is eccentrically located within outer lumen 142, ribs 252 only engage the inner wall of the outer lumen 142 with linear contact.

Figure 13:
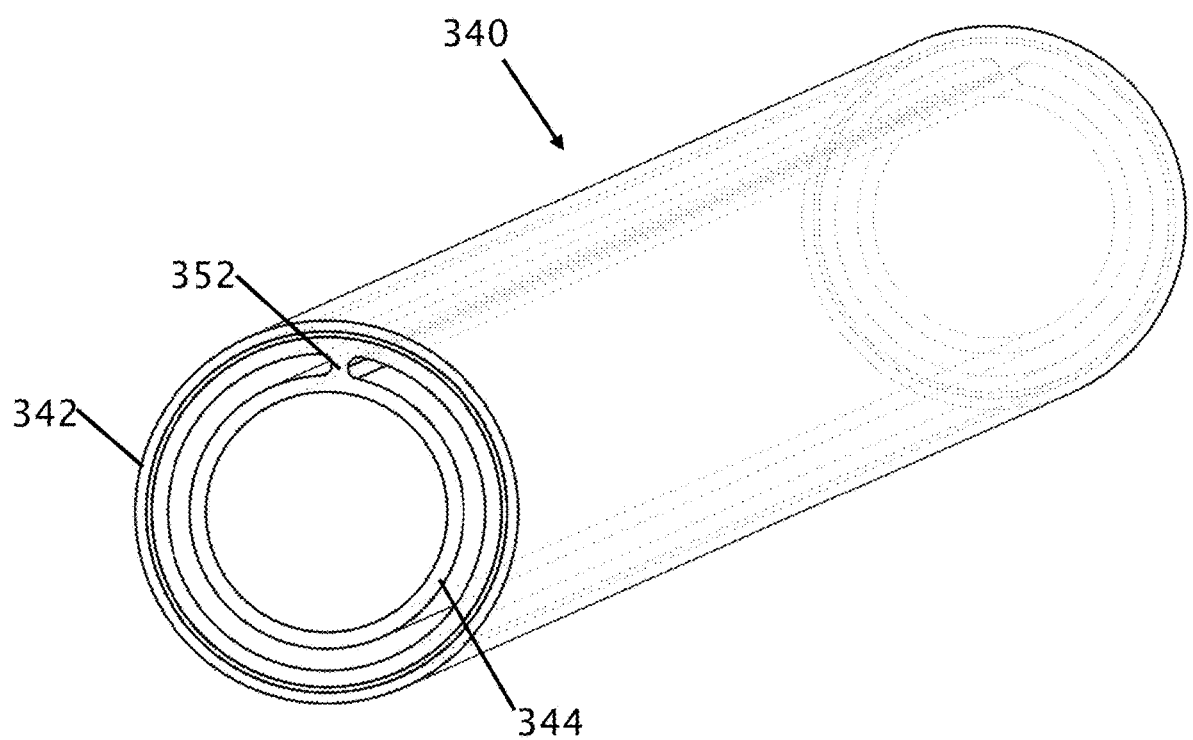
FIG. 13 is a perspective view of the distal end of the catheter of FIG. 4, with a third exemplary embodiment of an inner lumen inserted within the outer lumen.
Figure 14:
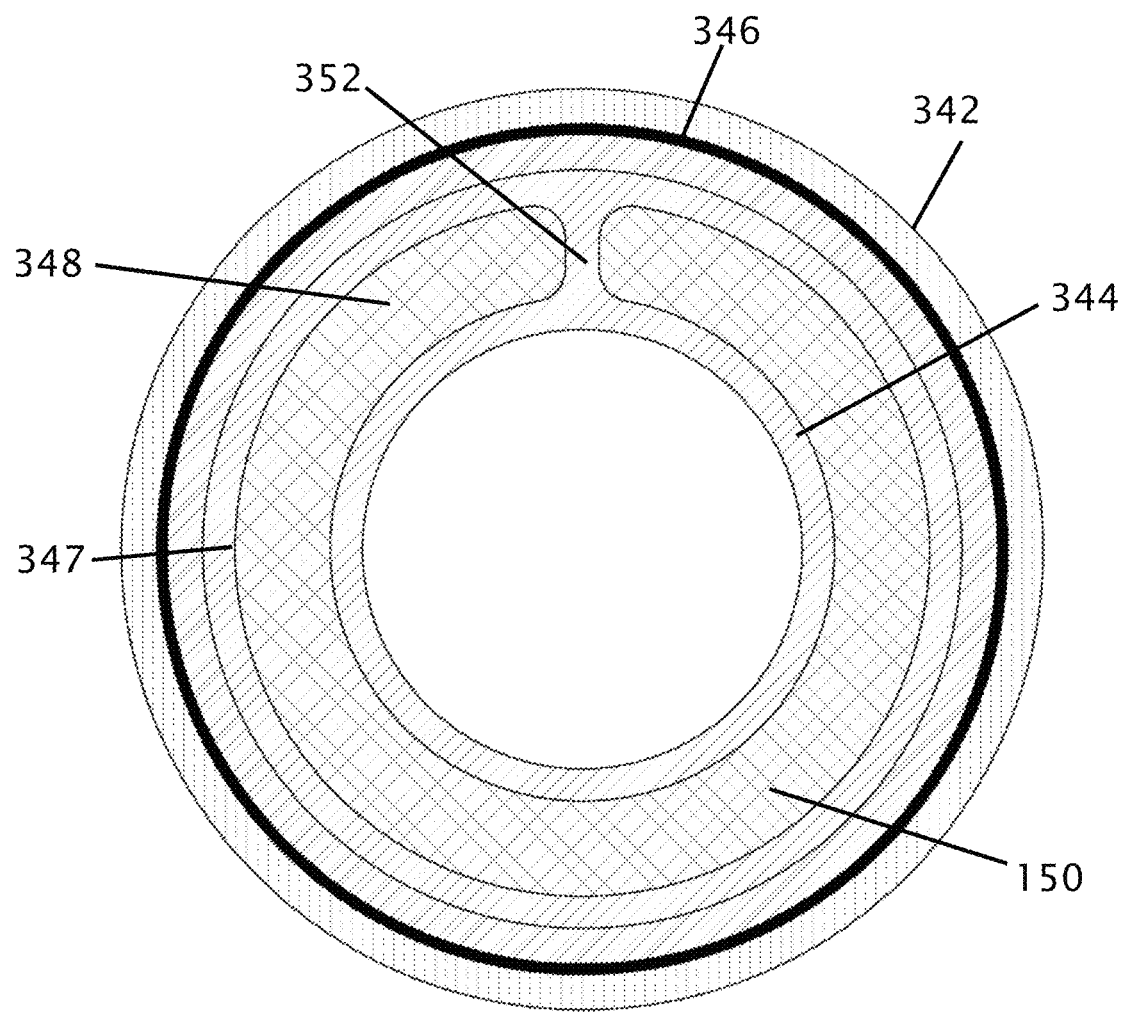
FIG. 14 is a distal elevational view of the catheter of FIG. 13, showing the inner lumen of FIG. 13 centrally located within the outer lumen.

Another alternative embodiment of a catheter body 340 is shown in FIGS. 13 and 14. Catheter body 340 includes an outer lumen 342 with a reinforcing coil 346 and an inner liner 347. With this embodiment, inner lumen 344 is physically connected to outer lumen 342 via a single rib 352 that extends the length of inner lumen 344. While heat conduction from outer lumen 342 to inner lumen 344 is conceded via rib 352, rib 352 maintains a generally constant centered positioning of inner lumen 344 within the space 348, thereby eliminating any additional heat conduction pathways directly between the outer lumen 342 and the inner lumen 344.

Figure 15:
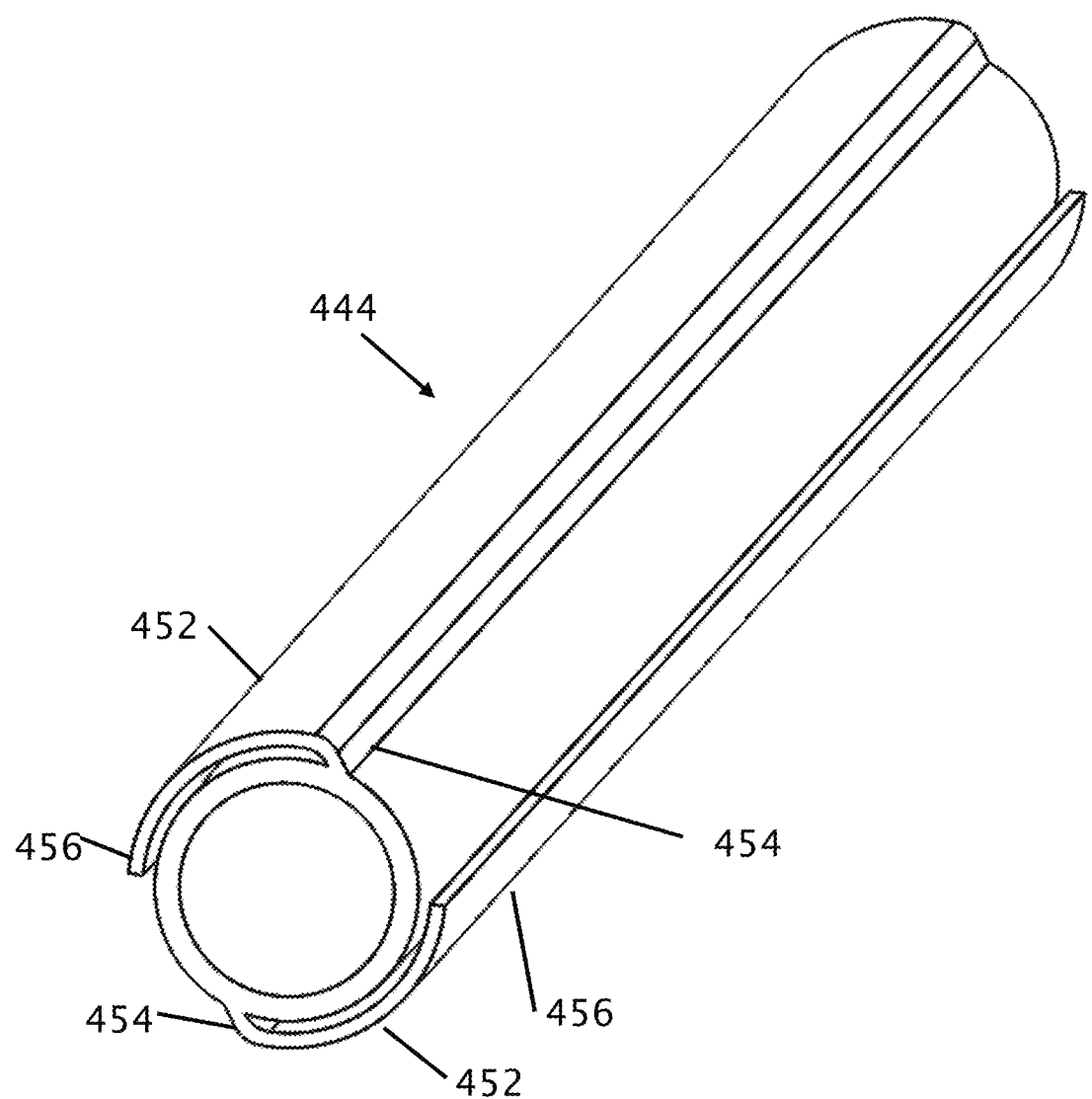
FIG. 15 is a perspective view of a fourth exemplary embodiment of an inner lumen for insertion within the outer lumen.
Figure 16:
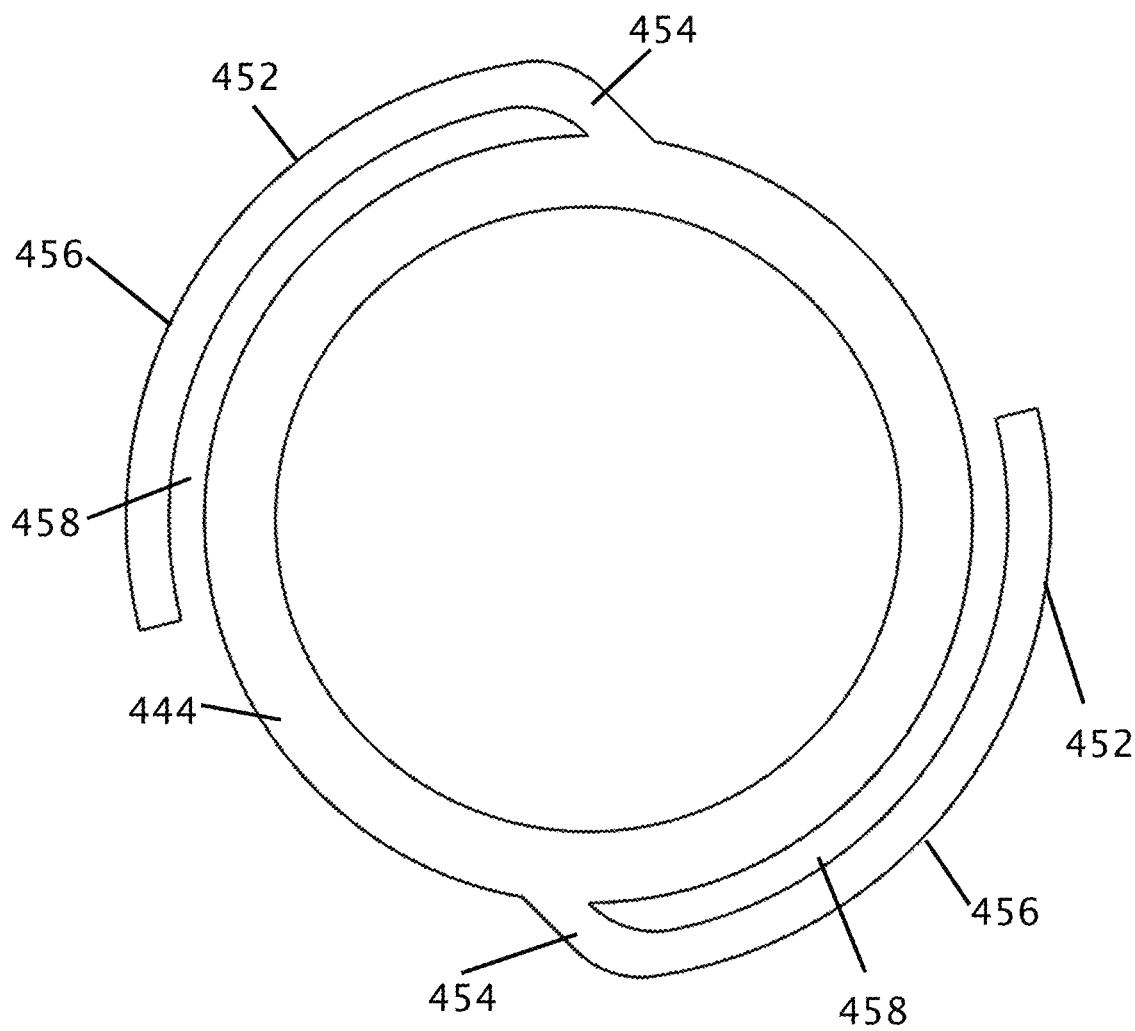
FIG. 16 is a distal elevational view of the inner lumen of FIG. 15.

Still another alternative embodiment of an inner lumen 444 is shown in FIGS. 15 and 16. Inner lumen 444 includes a pair of diametrically spaced arms assemblies 452 having a connection end 454 that extends obliquely away from inner lumen 444 and an arm 456 that radially extends from connection end 454 over an arc of about 90 degrees, leaving a void 458 between inner lumen 444 and arm 456.

While heat conduction from an outer lumen (not shown) to inner lumen 444 is conceded via arms 456, arms 456 bias inner lumen 444 away from the outer lumen, thereby maintaining a generally constant centered positioning of inner lumen 444 within outer lumen 142, and eliminating any other potential heat conduction pathways directly between the outer lumen 142 and the inner lumen 444.

Figure 17:
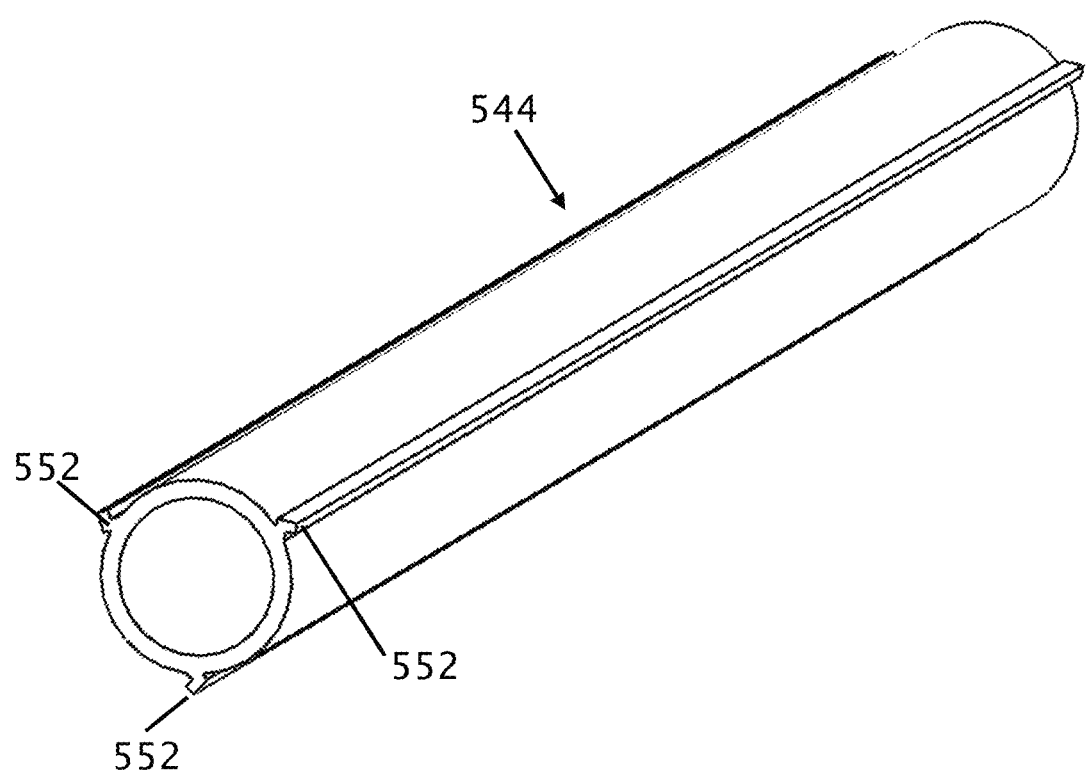
FIG. 17 is a perspective view of a fifth exemplary embodiment of an inner lumen for insertion within the outer lumen.
Figure 18:
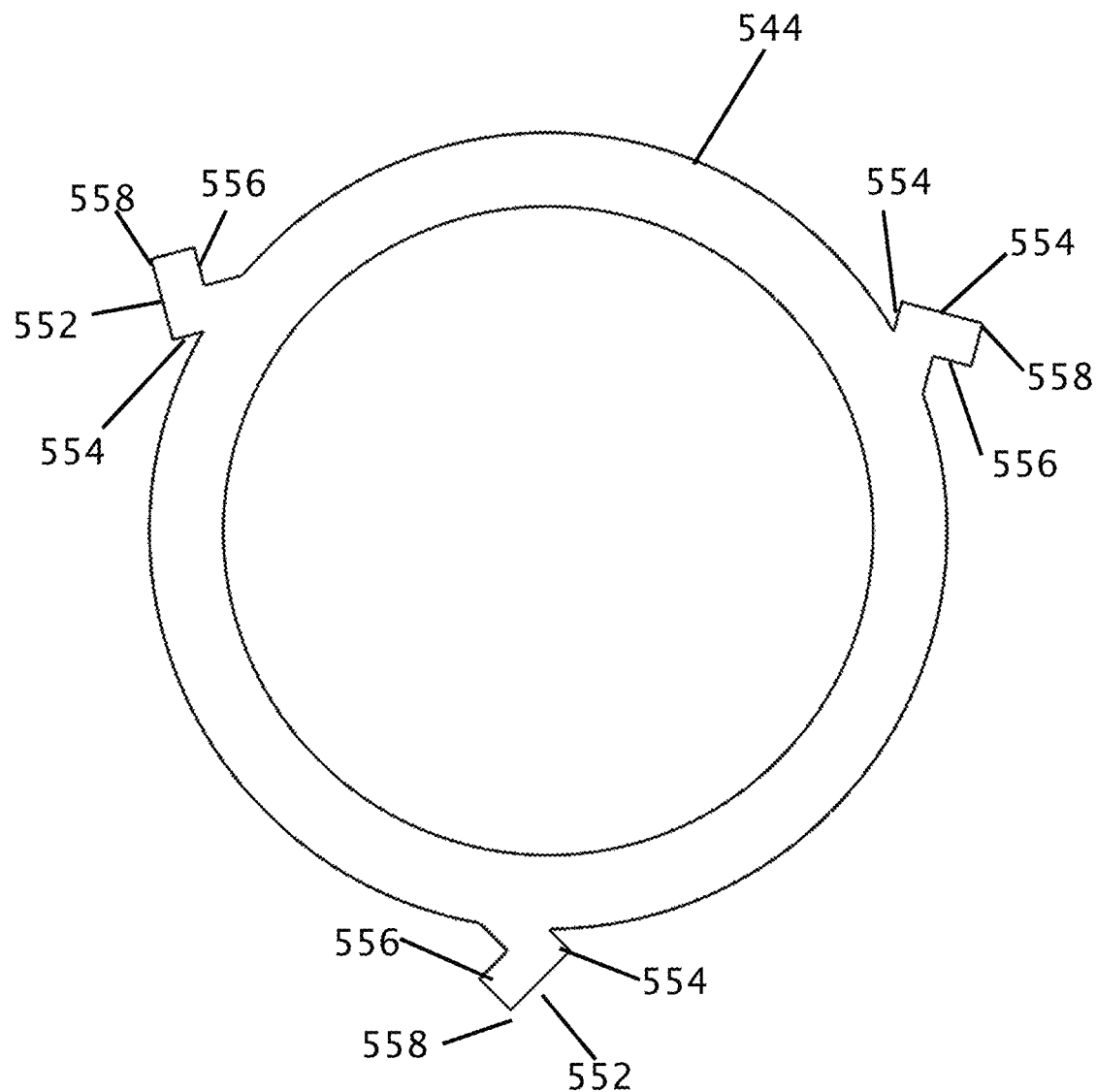
FIG. 18 is a distal elevational view of the inner lumen of FIG. 17.

Still another alternative embodiment of an inner lumen 544 is provided in FIGS. 17 and 18. Similar to inner lumen 144, inner lumen 544 can have a small enough outer diameter relative to the inner diameter of outer lumen 142 (not shown in FIGS. 17 and 18) such that inner lumen 544 can "float" within outer lumen 142. Ideally, inner lumen 544 is centered inside outer lumen 142 to minimize heat transfer. However, in reality, inner lumen 544 will likely engage the inner wall of outer lumen 142, resulting in at least some conductive heat transfer between the lumens 142, 544. To minimize the amount of contact area, inner lumen 544 can include a plurality of tangs 552 extending radially outwardly from inner lumen 544.

Tangs 552 each have a connection end 554, shown in FIG. 18, that extends obliquely away from inner lumen 544 and an arm 556 that radially extends from connection end 554. Each arm 556 ends in a corner edge 558. As shown in FIG. 17, tangs 552 can extend the entire length of inner lumen 544. Alternatively, tangs 552 can extend in smaller sections along the length of inner lumen 544, with distances along the length of inner lumen 544 that are free of any tangs 552. In an exemplary embodiment, three tangs 552 are provided and are evenly spaced about 120 degrees such that, in the event that inner lumen 544 is eccentrically located within outer lumen 142, at most, only corner edges 558 of two of the tangs 552 engage the inner wall of outer lumen 142, thereby minimize the area of contact between inner lumen 544 and outer lumen 142, and minimizing heat transfer from outer lumen 142 to inner lumen 544.

Figure 19:
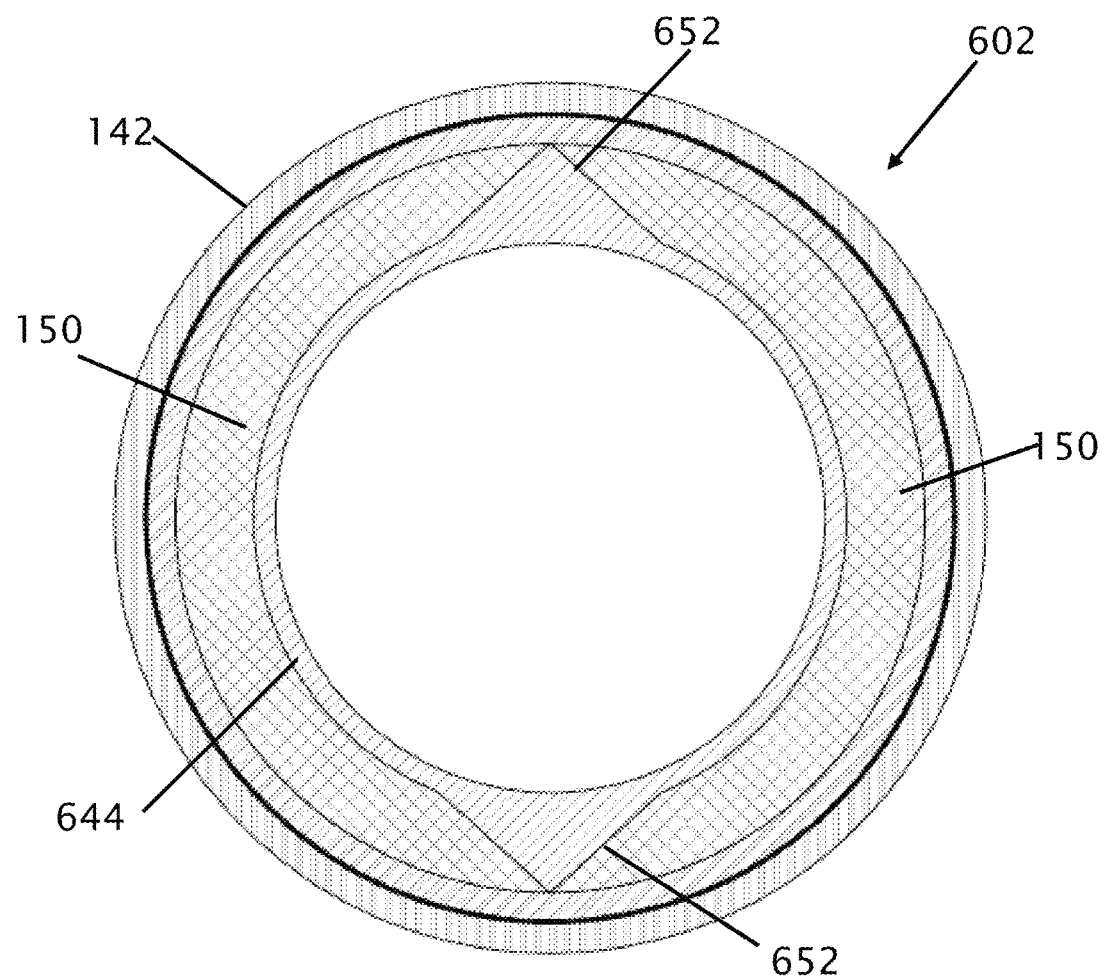
FIG. 19 is a distal elevational view of a sixth exemplary embodiment of an inner lumen inserted into the outer lumen.
Figure 20:
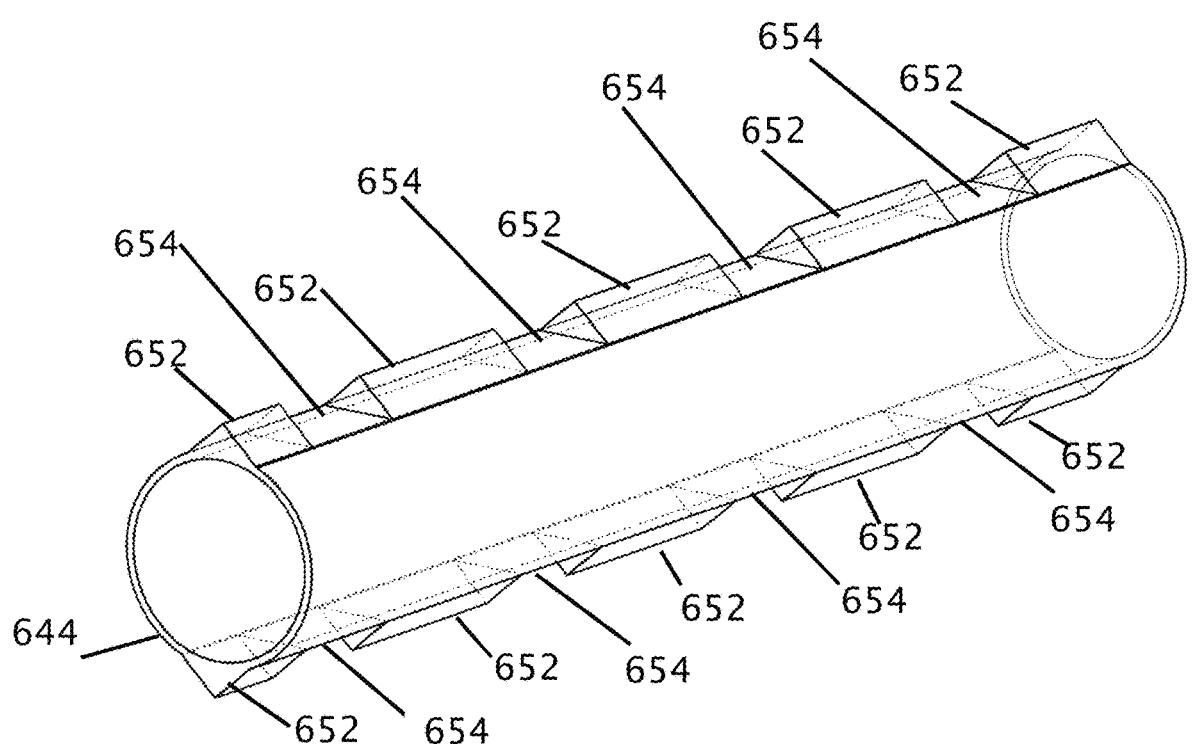
FIG. 20 is a side elevational view, in section, of the inner lumen of FIG. 19.

FIGS. 19 and 20 show an inner lumen 644 having diametrically opposed ribs 652 with triangular shaped cross sections. Ribs 652 have a generally triangular cross section. Inner lumen 644 and ribs 652 are sized so that ribs 652 engage outer lumen 142, thereby generally centering inner lumen 644 within the space 148. As shown in FIG. 20, ribs 652 are segmented, with spaces 654 between adjacent ribs 652 on either side of inner lumen 644 to reduce contact area with outer lumen 142, thereby reducing conductive heat transfer between the outer lumen 142 and the inner lumen 644.

For all of the embodiments of inner lumens 144-644 described above, the distal end of the inner lumen 144-644 is attached to the distal tip 160 such that the inside of the inner lumen 144-644 is in fluid communication with the tip 160.

Further, while ribs, arms, and other structures extending outwardly from inner lumens 144-644 are shown, those skilled in the art will recognize that other structures for centering the inner lumens within their respective outer lumens can be used. Further, such structures can extend inwardly from the outer lumens 142 instead of or in addition to the structures extending outwardly from the inner lumens.

Referring back to FIGS. 4 and 5, optionally, a vacuum port assembly 120 is used to draw at least a partial vacuum on space 148 to further reduce the thermal transfer to inner lumens 144-644 and further enhance the Knudsen effect of the catheter assembly 100. Thermal conductivity of the gas inside an aerogel is inversely dependent on the Knudsen number, Kn. This number, Kn, is defined as the ratio of the mean free path to the average pore size. When vacuums are applied at virtually any level, the mean free path increases, Kn increase, and the thermal conductivity in the gas inside the aerogel particles and the air surrounding the particles decreases. Vacuum port assembly 120 includes a central longitudinal axis 122 with a passage 124 extending along axis 122 from a proximal end 121 and in fluid communication with space 148 in body 140. Passage 124 intersects with space 148 at a hub juncture 126.

A filter 130 is located along axis 122 proximally of hub juncture 126. Filter 130 includes filter media fine enough to prevent the insulation, namely, aerogel, from being drawn out of space 148 during the vacuum process. A check valve 132 is located proximally of filter 130 to prevent air from flowing from atmosphere, through passage 124, and into space 148.

Any insulative approach will benefit from vacuum, however polymers are poor choices for medium vacuum (25 to 0.001 mmHg absolute). To reduce vacuum losses through the wall of the outer lumen, a thin metallic coating can be applied to sections of the catheter that are exposed to air to reduce ability of air to permeate the polymer. An exemplary method for applying metal to a polymer is the MetaPoly™ process, by ProPlate, wherein the bond between the polymer substrate and electroplated metal is comparable to a metal to metal atomically electroplated bond, which eliminates the adhesion issues experienced utilizing alternative methods. Although the medical device applications are limitless, the Meta-Poly™ process is especially exciting for catheter applications. For example, ProPlate® can selectively add radiopaque markers and current conducting paths to polymers. Meta-Poly™ provides the same benefits as plating on metallic surfaces; eliminates risk of dislodgment, maintains a low profile, offers cost reduction, and provides endless possibilities for design customization.

Figure 21:
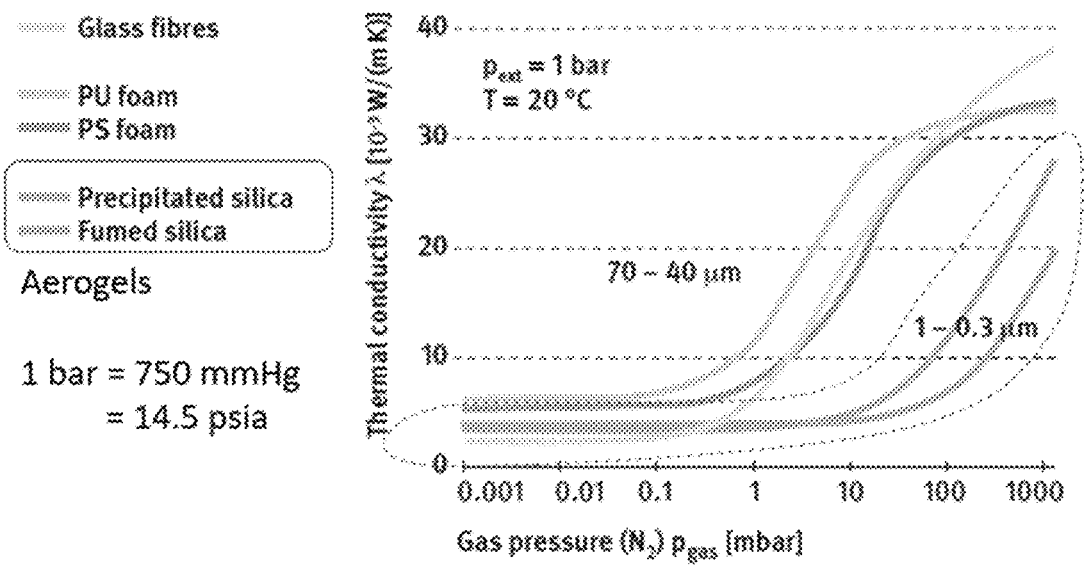
FIG. 21 is a graph of Insulative Quality v. Pressure for the inventive catheter assembly.

FIG. 21 shows how aerogel thermal conductivity changes with surrounding pressure; vacuum pressures ranging from 0.001 mbar to 1000 mbar or 1 atmosphere. Between about 0.001 mbar and about 10 mbar thermal conductivity is only between about $3 \times 10^{-3}$ W/(m-K) and about $4 \times 10^{-3}$ W/(m-K). The thermal insulation properties of aerogel are increased when the aerogel is a powder, which increases contact resistance; the aerogel is at low pressure (contact area drops and mean free path increases); and the aerogel has small pore sizes, leading to larger Knudsen numbers and small gas phase component. Optionally, an infrared opacifier can be added to the aerogel, reducing radiative heat transfer. Opacified or doped aerogels reduce radiative heat transfer by limiting the mean free path of photons.

Figure 22:
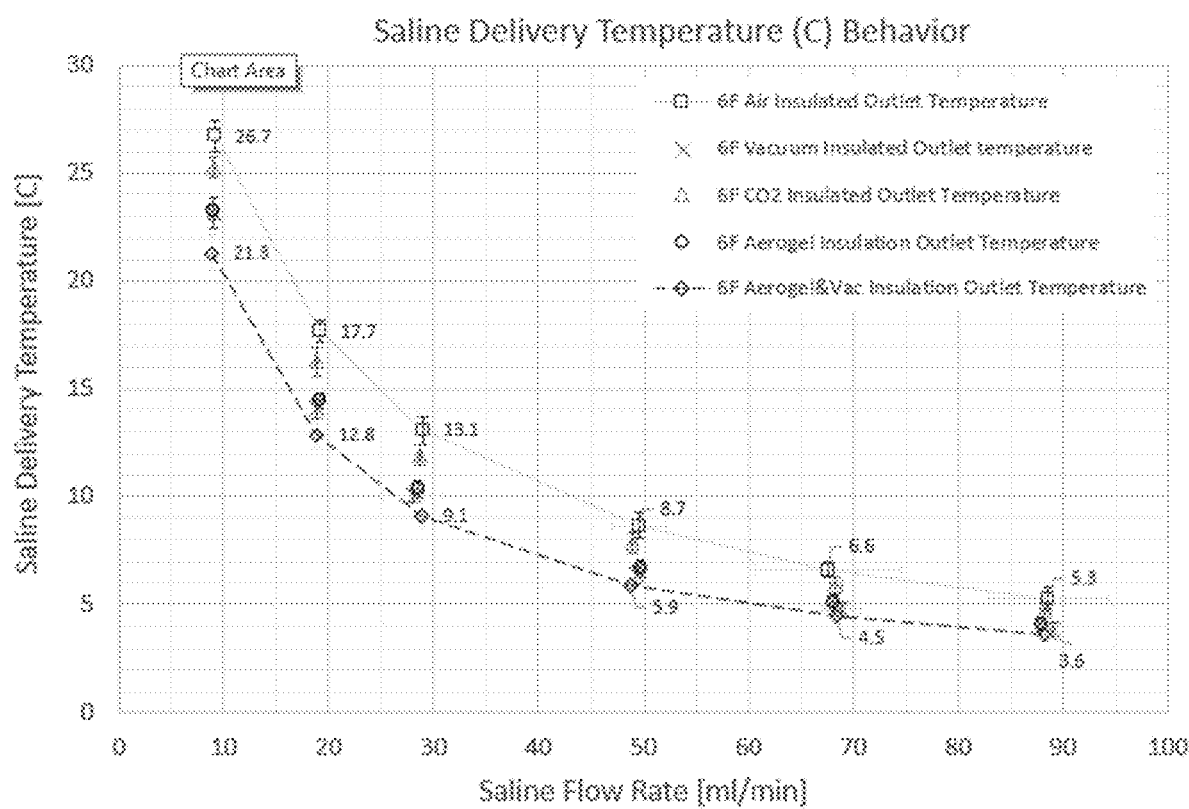
FIG. 22 is a plot of saline delivery temperature vs flow rate and insulation.

FIG. 22 is a plot of saline delivery temperature vs flow rate and insulation. This plot reveals the impact of insulation type on overall cooling capacity as function of flow rate. For all insulation types, slower delivery flow rates provide the least cooling since there is more time for heat transfer to occur, resulting in warmer delivery temperatures. Conversely, faster flow rates deliver greater cooling capacity. Most human studies thus far have used saline flow rates between 10 and 30 ml/min. Higher flow rates raise safety concerns regarding hemodilution, where the saline displaces oxygen-carrying red blood cells. The inventive Knudsen Effect catheter provides the coolest saline delivery temperatures.

Figure 23:
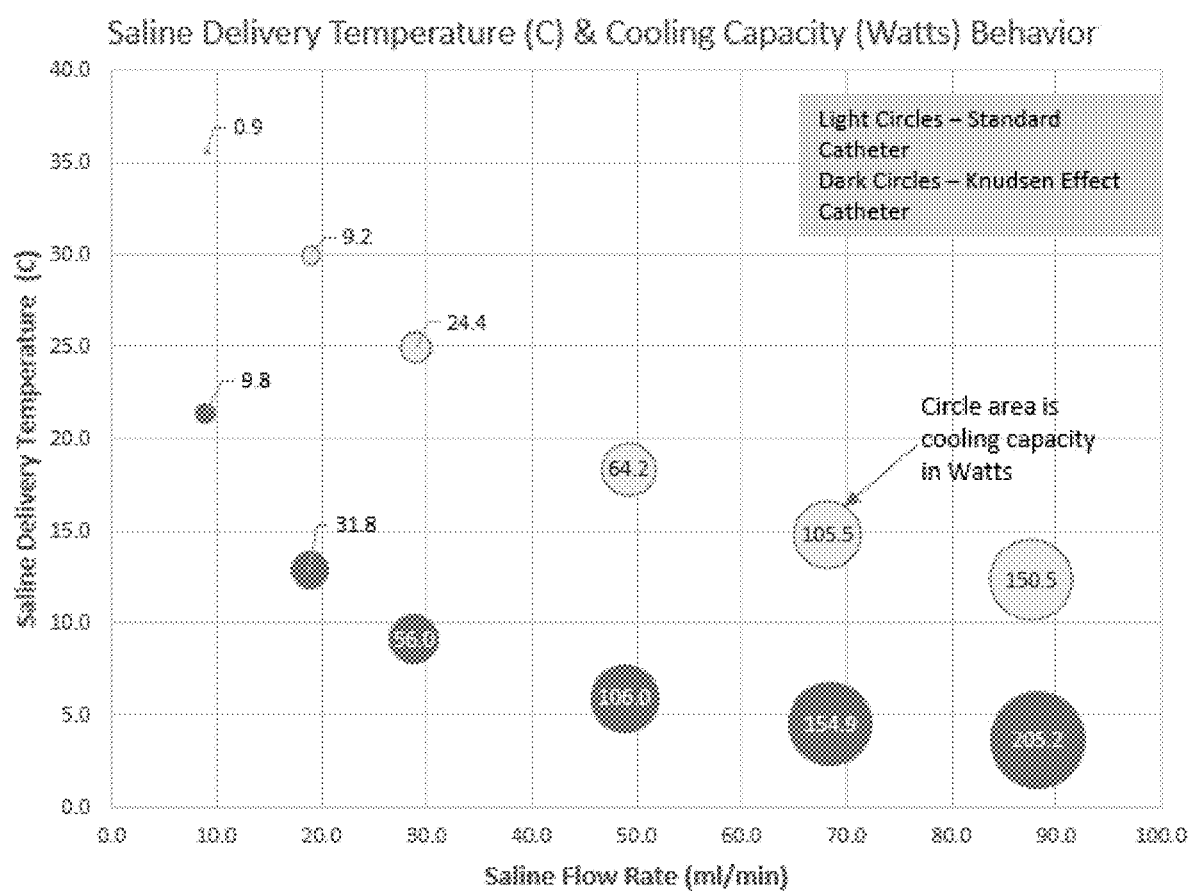
FIG. 23 is a plot of saline delivery temperature vs flow rate and catheter type.

FIG. 23 is a plot of saline delivery temperature vs flow rate and catheter type. This plot shows that the cooling capacity of the inventive Knudsen Effect catheter outperforms a standard catheter at all flow rates.

Figure 24:
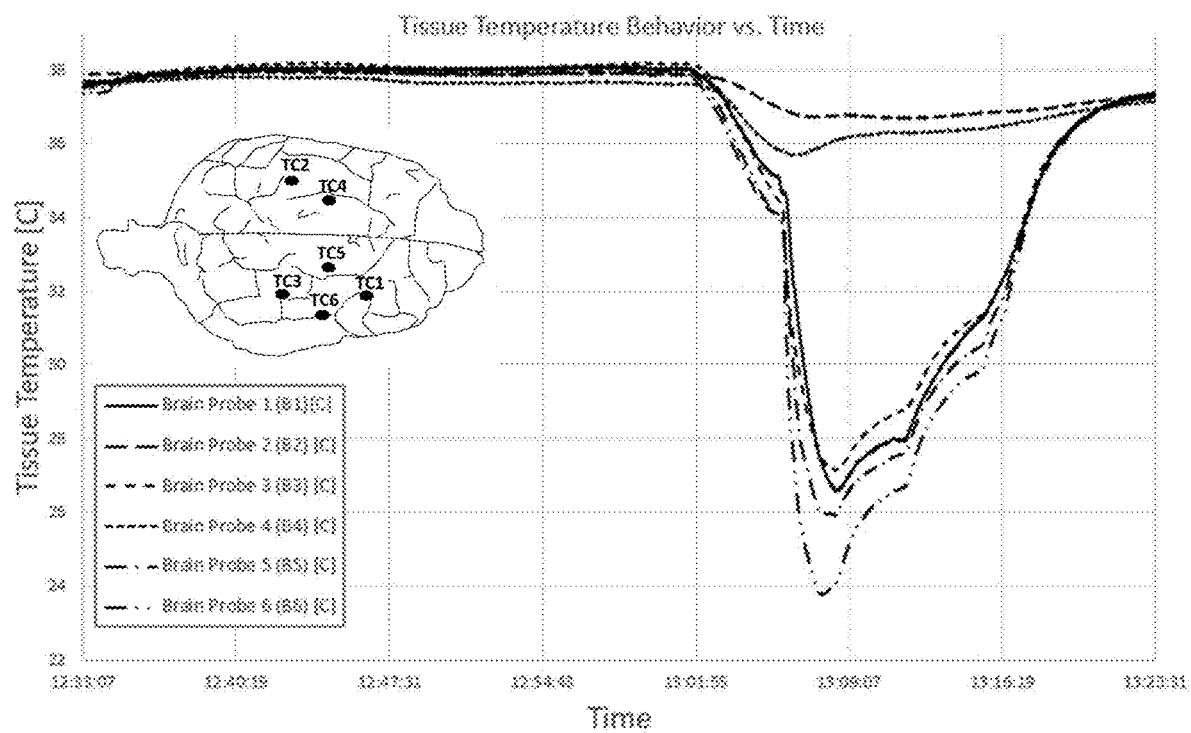
FIG. 24 is a plot of tissue temperature vs time for the inventive Knudsen Effect catheter.

FIG. 24 is a plot of tissue temperature vs time for the inventive Knudsen Effect catheter. This plot shows the tissue temperature response as a function of time. Six brain probes are used to show how temperature varies within the brain. Cooling begins at 13:01:55 at a delivery flow rate that varies from 0 to 35 ml/min over a span of 5 minutes. At approximately 13:07:00, reperfusion occurs and the flow rate is reduced to 22 ml/min. Cooling is maintained at 22 ml/min for approximately 20 minutes and then followed by ramped reduction of cooling flow rate for 5 minutes (22 ml/min to 0 ml/min).

In the case where heat transfer in aerogels depends on the local temperature gradient, the effective total thermal conductivity $\lambda_{\mathit{eff}}$ can be expressed as the sum of the solid thermal conductivity of the solid backbone $\lambda_s$, the effective thermal conductivity of the gaseous phase $\lambda_g$, and finally, the radiative conductivity $\lambda_r$, as calculated in the equation:

$$\lambda_{\mathit{eff}}(T,p_g) = \lambda_s(T) + \lambda_g(T,p_g) + \lambda_r(T)$$

The distal tip 160 of the catheter assembly 100 is where the infusate emerges, cooled and prepared to reduce organ tissue temperatures. In an exemplary embodiment, the distal tip 160 can be a low durometer (super flexible) Pebax®, such as a 25D with 20% $BaSO_4$ (added for radiopacity). The distal tip 160 includes a passage 162 (shown in FIG. 4) through inner lumen 144 that allows the infusate or other device to exit the catheter assembly 100. Outer lumen 142 has a closed distal end to retain insulating material in the space 148 between inner lumen 144 and outer lumen 142.

For myocardial infarction treatment, the tip 160 can be placed at the ostium of the heart or within the small coronary arteries 56. Tip 160 is radiopaque to allow visualization of the location of tip 160 via radiographic means. For brain cooling, the tip 160 can be placed in the carotid, inner carotid, or middle cerebral arteries.

To use catheter assembly 100, catheter assembly 100 is inserted into a patient's blood vessel according to known methods and advanced to an area where cooling is desired/required. The radiopaque tip 160 allows the interventionist to see where the tip 160 is located in the patient. The infusate supply is connected to the proximal end 114 of hub 110 and pumped through the catheter body 140 to the distal tip 160, out the distal tip 160, and to the desired location in the patient.

Optionally, prior to injecting the infusate through the catheter assembly 100 to the treatment location in the patient, the vacuum can be drawn on space 148 by connecting a syringe or vacuum pump (not shown) to the vacuum port assembly 120 at proximal end 121.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A flexible insulative endovascular guiding catheter, comprising:
    an outer lumen, tubular in cross section, having an outer lumen proximal end and an outer lumen distal end separated by an outer lumen length, the outer lumen having an outer lumen inner diameter which extends along the outer lumen length and an outer lumen outer diameter configured to at least pass coaxially within a guide catheter;
    an inner lumen, non-circular in cross section, having an inner lumen proximal end having an inner lumen proximal end opening and an inner lumen distal end having an inner lumen distal end opening separated by an inner lumen length, the inner lumen having an inner lumen outer profile and an inner lumen inner diameter each extending along the inner lumen length,
    the inner lumen inner diameter configured to at least pass coaxially a microcatheter through the inner lumen proximal end opening which passes through the inner lumen and out of the inner lumen distal end opening;
    the inner lumen outer profile being smaller than the outer lumen inner diameter;
    the inner lumen having at least a portion of the inner lumen length disposed within at least a portion of the outer lumen along at least a portion of the outer lumen length,
    an eccentric annular space between the inner lumen outer profile and the outer lumen inner diameter which extends along an eccentric annular space length from a proximal eccentric annular space end to a distal eccentric annular space end, the eccentric annular space length extending along at least a portion of the inner lumen length and extending along at least a portion of the outer lumen length;
    the distal eccentric annular space end being a closed end proximal to a distal tip, the closed end retaining an insulating material in the eccentric annular space;
    a hub configured to feed at least a microcatheter to the inner lumen,
    the hub and the proximal eccentric annular space end configured to retain the insulating material in the eccentric annular space;
    the insulating material disposed within the eccentric annular space configured to insulate the inner lumen from heat transfer from the outer lumen;
    the insulating material filling at least a portion of the eccentric annular space;
    the inner lumen configured at least in part to provide discontiguous contact between the inner and outer lumen without substantially affecting the catheter flexibility;
    a plurality of ribs extending radially from the inner lumen into the eccentric annular space configured to control the eccentric annular space configuration and the heat transfer from the outer lumen to the inner lumen.

2. The catheter of claim 1, wherein the plurality of ribs is a group of three ribs spaced about 120 degrees equally apart along the inner lumen outer profile.

3. The catheter of claim 1, wherein the plurality of ribs contacts the outer lumen inner diameter only on corner edges of the ribs.

4. The catheter of claim 1 wherein said outer lumen proximal end has a metallic plating configured to retain the insulating material in the eccentric annular space.

* * * * *